(12) United States Patent
Kollias et al.

(10) Patent No.: US 7,404,815 B2
(45) Date of Patent: Jul. 29, 2008

(54) TISSUE ABLATION BY SHEAR FORCE FOR SAMPLING BIOLOGICAL FLUIDS AND DELIVERING ACTIVE AGENTS

(75) Inventors: Nikiforos Kollias, Skillman, NJ (US);
Ying Sun, Somerville, NJ (US);
Anthony F. Coston, Stockton, NJ (US)

(73) Assignee: Lifescan, Inc., Milpitas, CA (US)

( * ) Notice: Subject to any disclaimer, the term of this patent is extended or adjusted under 35 U.S.C. 154(b) by 1132 days.

(21) Appl. No.: 09/845,956

(22) Filed: Apr. 30, 2001

(65) Prior Publication Data

US 2002/0058902 A1     May 16, 2002

(51) Int. Cl.
*A61M 31/00*     (2006.01)

(52) U.S. Cl. .......................... 604/501; 604/20

(58) Field of Classification Search ......... 604/500–501, 604/20, 22, 46–47, 890.1, 272, 503–505, 604/65–67; 600/573, 583, 309, 873
See application file for complete search history.

(56) References Cited

U.S. PATENT DOCUMENTS

| | | | |
|---|---|---|---|
| 3,315,665 A | 4/1967 | MacLeod | |
| 3,950,158 A | 4/1976 | Gossett | |
| 3,964,482 A | 6/1976 | Gerstel et al. | |
| 4,230,105 A | 10/1980 | Harwood | |
| 4,406,658 A * | 9/1983 | Lattin et al. ................. | 604/20 |
| 4,655,766 A | 4/1987 | Theeuwes et al. | |
| 4,685,911 A | 8/1987 | Konno et al. | |
| 4,767,402 A | 8/1988 | Kost et al. | |
| 4,790,824 A | 12/1988 | Morrow et al. | |
| 4,963,360 A | 10/1990 | Argaud | |
| 5,013,293 A | 5/1991 | Sibalis | |
| 5,036,861 A | 8/1991 | Sembrowich et al. | |
| 5,042,975 A | 8/1991 | Chien et al. | |
| 5,127,163 A | 7/1992 | Locke | |
| 5,135,478 A | 8/1992 | Sibalis | |
| 5,156,591 A | 10/1992 | Gross et al. | |
| 5,213,568 A | 5/1993 | Lattin et al. | |
| 5,224,927 A | 7/1993 | Tapper | |
| 5,250,023 A | 10/1993 | Lee et al. | |
| 5,279,543 A | 1/1994 | Glikfeld et al. | |
| 5,279,544 A | 1/1994 | Gross et al. | |
| 5,320,607 A | 6/1994 | Ishibashi | |

(Continued)

FOREIGN PATENT DOCUMENTS

DE     195 25 607 A1     7/1995

(Continued)

OTHER PUBLICATIONS

Sun, Y. (1997) Skin Absorption Enhancement by Physical Means: Heat, Ultrasound, and Electricity. Transdermal and Topical Drug Delivery Systems.327-355.

(Continued)

*Primary Examiner*—Nicholas D. Lucchesi
*Assistant Examiner*—Theodore J Stigell

(57) ABSTRACT

The present invention relates to a method and a device for transporting a molecule through a mammalian barrier membrane of at least one layer of cells comprising the steps of: ablating said membrane with a shear device; and utilizing a driving force to move said molecule through said perforated membrane.

24 Claims, 13 Drawing Sheets

U.S. PATENT DOCUMENTS

| | | |
|---|---|---|
| 5,362,307 A | 11/1994 | Guy et al. |
| 5,386,837 A | 2/1995 | Sterzer |
| 5,399,163 A | 3/1995 | Peterson et al. |
| 5,438,984 A | 8/1995 | Schoendorfer |
| 5,441,490 A * | 8/1995 | Svedman .................. 604/289 |
| 5,527,288 A | 6/1996 | Gross et al. |
| 5,533,971 A | 7/1996 | Phipps |
| 5,540,669 A | 7/1996 | Sage, Jr. et al. |
| 5,582,586 A | 12/1996 | Tachibana et al. |
| 5,591,124 A | 1/1997 | Phipps |
| 5,614,502 A | 3/1997 | Flotte et al. |
| 5,636,632 A | 6/1997 | Bommannan et al. |
| 5,658,583 A | 8/1997 | Zhang et al. |
| 5,658,892 A | 8/1997 | Flotte et al. |
| 5,662,624 A | 9/1997 | Sundstrom et al. |
| 5,667,491 A | 9/1997 | Pliquett et al. |
| 5,718,955 A | 2/1998 | McGuire et al. |
| 5,853,383 A | 12/1998 | Murdock |
| 5,857,992 A | 1/1999 | Haak et al. |
| 5,885,211 A | 3/1999 | Eppstein et al. |
| 5,983,136 A * | 11/1999 | Kamen .................. 604/21 |
| 6,048,337 A | 4/2000 | Svedman |
| 6,050,988 A | 4/2000 | Zuck |
| 6,083,196 A | 7/2000 | Trautman et al. |
| 6,104,952 A | 8/2000 | Tu et al. |
| 6,132,755 A | 10/2000 | Eicher et al. |
| 6,219,574 B1 * | 4/2001 | Cormier et al. ............... 604/20 |
| 6,678,554 B1 * | 1/2004 | Sun et al. ..................... 604/20 |

FOREIGN PATENT DOCUMENTS

| | | |
|---|---|---|
| EP | 0 429 842 A2 | 10/1990 |
| EP | 429842 A2 * | 6/1991 |
| GB | 2 303 208 A | 2/1997 |
| WO | 86/07269 A1 | 12/1986 |
| WO | WO 8901338 A1 * | 2/1989 |
| WO | 92/07618 A1 | 5/1992 |
| WO | 93/17754 A1 | 9/1993 |
| WO | 94/23777 A1 | 10/1994 |
| WO | 95/30410 A3 | 11/1995 |
| WO | 96/00110 A1 | 1/1996 |
| WO | 96/17648 A1 | 6/1996 |
| WO | 96/37256 A1 | 11/1996 |
| WO | 97/04832 A1 | 2/1997 |
| WO | 97/12644 A1 | 4/1997 |
| WO | 97/48440 A1 | 12/1997 |
| WO | 97/48441 A1 | 12/1997 |
| WO | 97/48442 A1 | 12/1997 |
| WO | 98/11937 A1 | 3/1998 |
| WO | 98/28037 A1 | 3/1998 |
| WO | 98/28038 A1 | 7/1998 |
| WO | 98/29134 A2 | 7/1998 |
| WO | 98/46124 A1 | 10/1998 |

OTHER PUBLICATIONS

Buyuktimkin N., Buyuktimkin S. (1997) Chemical Means of Transdermal Drug Permeation Enhancement. Transdermal and Topical Drug Delivery Systems. 357-475.

Sun Y., Liu J.C., Xue H. Important Parameters Affecting Iontophoretic Transdermal Delivery of Insulin. Proceed. Intern. Symp. Control. Rel. Bioact. Mater., 17, Controlled Release Society, Inc. (1990) 202-203.

Roberts M. Lai P., Cross S., Yoshida N. (1997) Solute Structure as a Determinant of Iontophoretic Transport. Mechanisms of Transdermal Drug Delivery. 291-349.

Remington MicroScreen product and product packaging 1999.

Panasonic Cordless Shaver ad 2000.

Panasonic Sonic Shaving-Linear ad 2000.

Remington Microscreen 1 cordless shaver product data 1999.

Johnson & Johnson Consumer Companies, Inc., pending U.S. Appl. No. 09/385,284.

Johnson & Johnson Consumer Companies, Inc., pending U.S. Appl. No. 09/644,093.

Johnson & Johnson Consumer Companies, Inc., pending U.S. Appl. No. 09/611,865.

Johnson & Johnson Consumer Companies, Inc., pending U.S. Appl. No. 09/612,357.

Johnson & Johnson Consumer Companies, Inc., pending U.S. Appl. No. 09/795,908.

Johnson & Johnson Consumer Companies, Inc., pending U.S. Appl. No. 09/548,771.

Johnson & Johnson Consumer Companies, Inc., Pending U.S. Appl. No. 09/549,147.

* cited by examiner

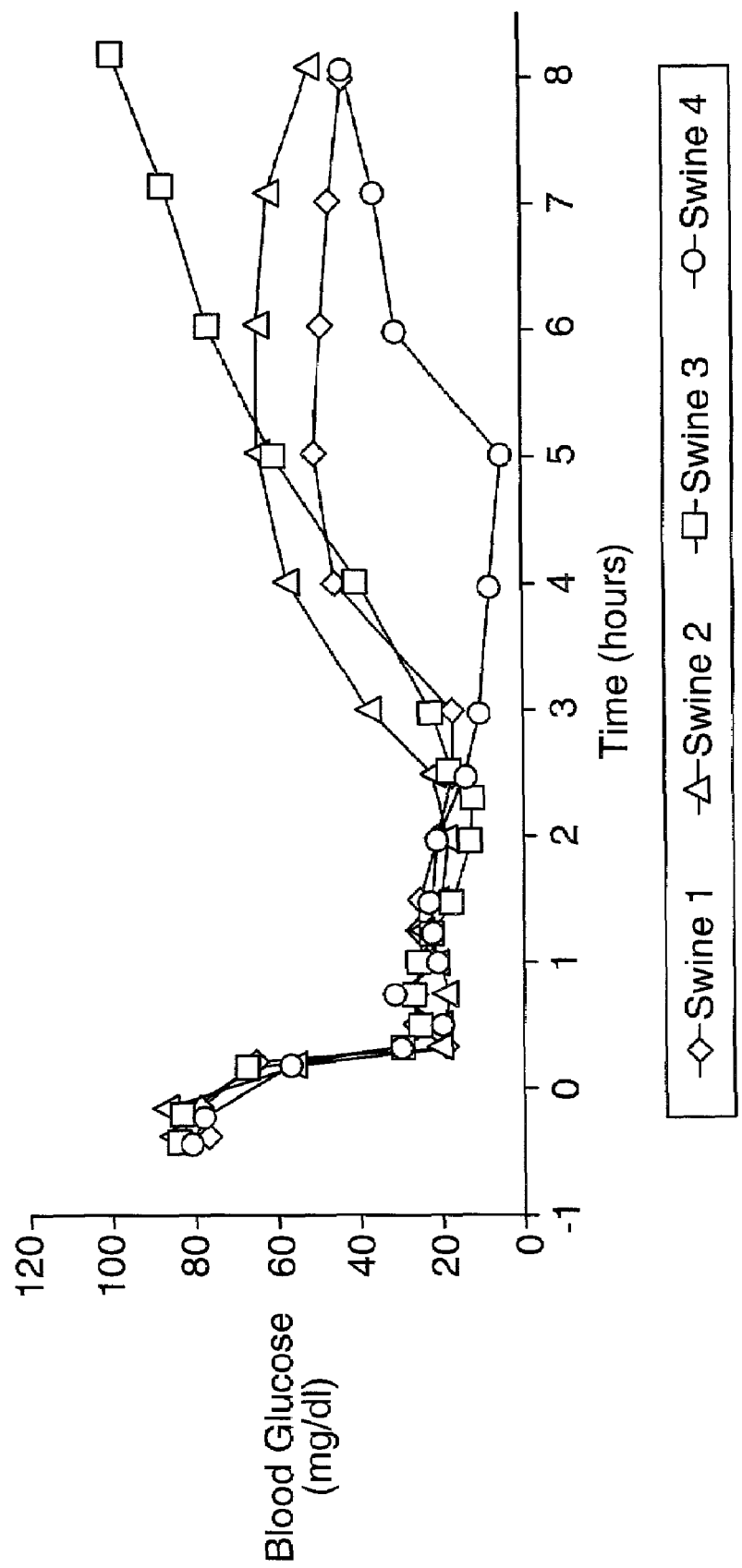

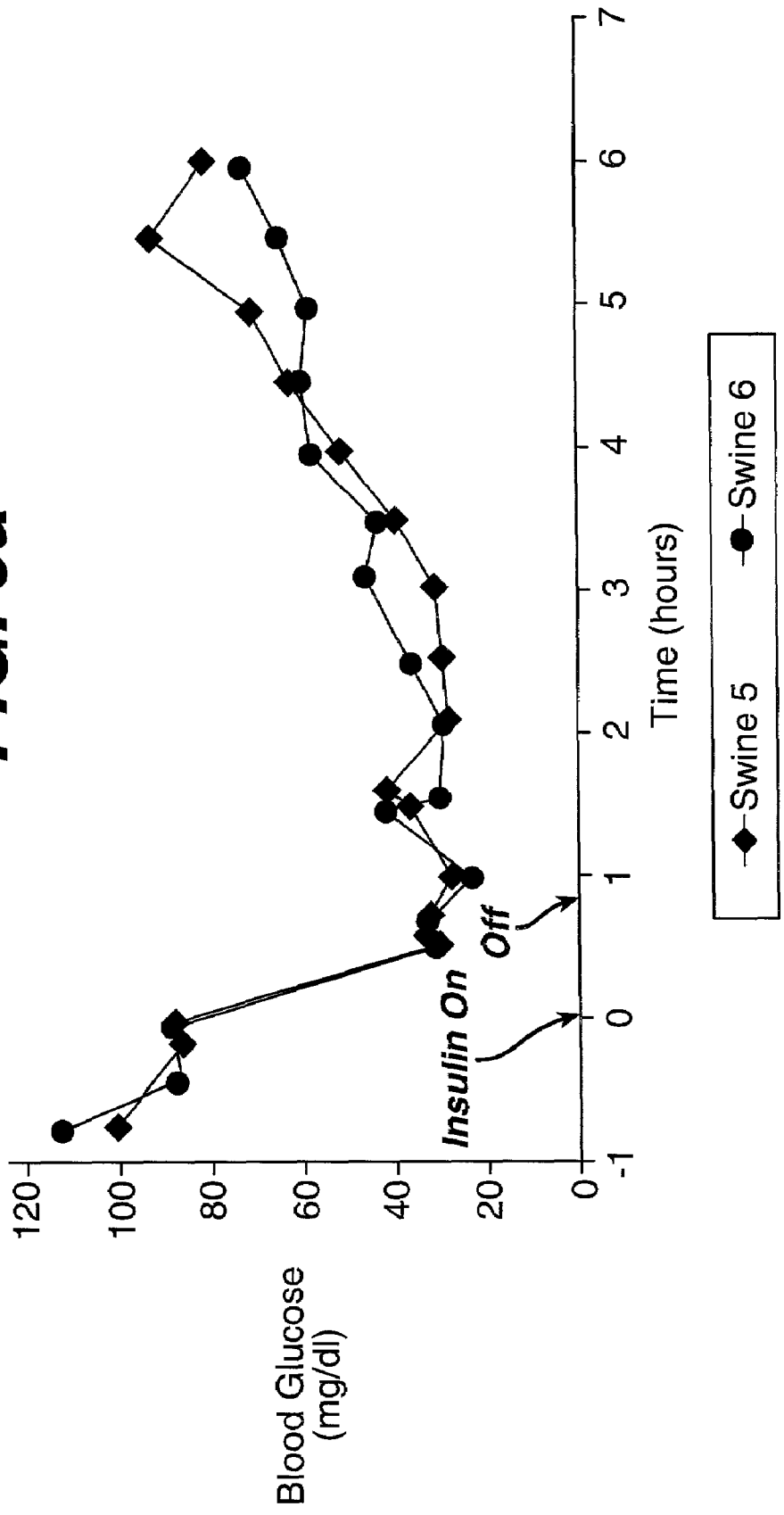

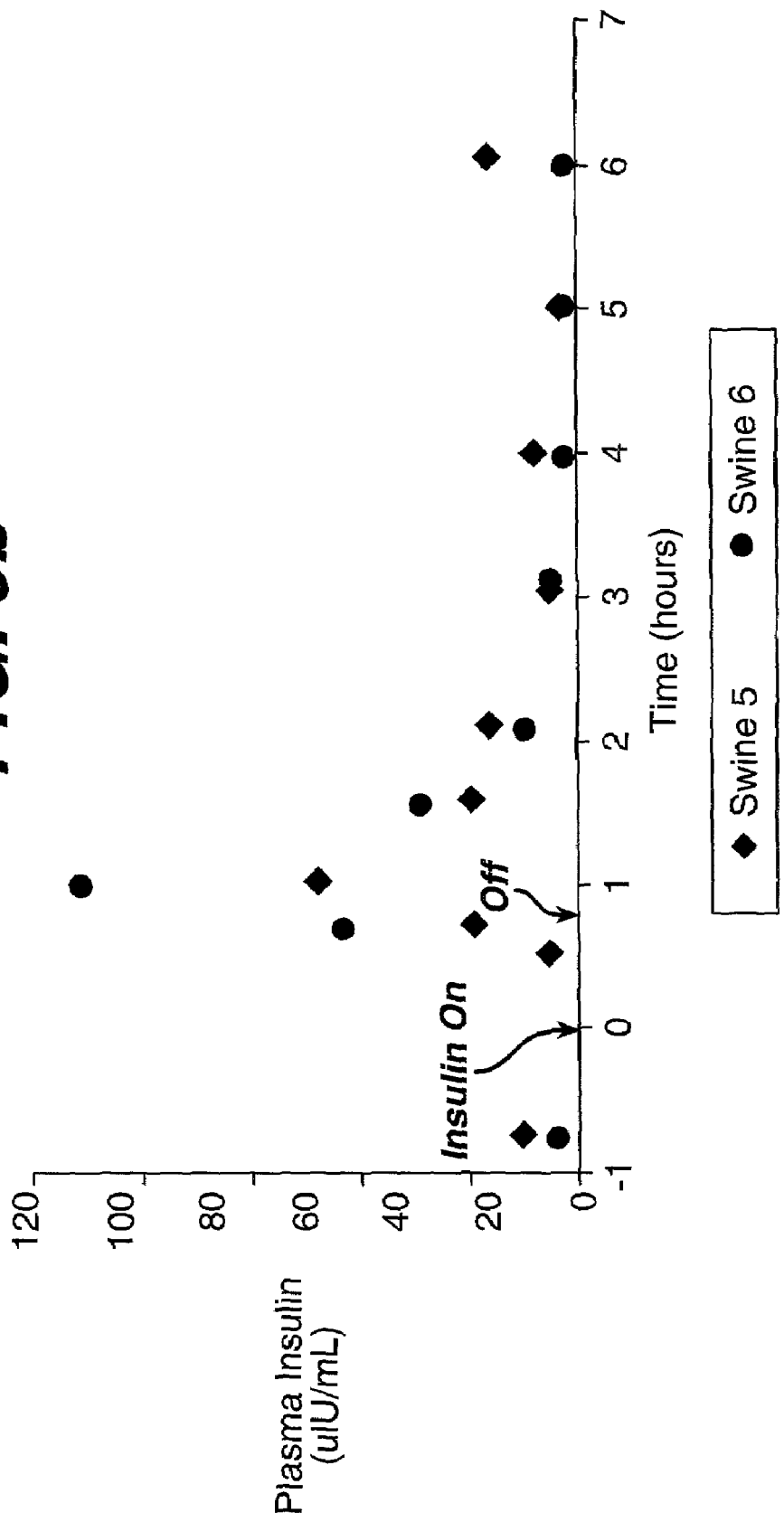

TISSUE ABLATION BY SHEAR FORCE FOR SAMPLING BIOLOGICAL FLUIDS AND DELIVERING ACTIVE AGENTS

FIELD OF THE INVENTION

The present invention relates to methods and devices for the ablation of barrier membranes using a shear device in order to enable sampling of biological fluids for diagnostic purposes and to enable delivering of active compounds for therapeutic purposes.

BACKGROUND OF THE INVENTION

Many medical procedures in use today require a relatively small sample of blood (e.g., 5-50 micro-liters) This blood is often obtained by lancing or piercing the skin (e.g., of the finger) with a needle of a spring-loaded lancet to enable the collection of 1 or 2 drops of blood. See, e.g., U.S. Pat. Nos. 4,503,856 and 4,517,978. This lancing procedure, however, can be quite painful due to the highly sensitive skin at the fingers. Furthermore, to facilitate the blood collection, some forms of pressure gradients, such as either applying a positive pressure (e.g., by squeezing) or a negative pressure (i.e., a suction), is often required to be applied to the cut. See, e.g., U.S. Pat. Nos. 4,637,403, 4,654,513, 5,320,607, and 5,368, 047.

Unfortunately, diabetic patients have to endure this painful lancing procedures several times a day, in addition to insulin injections, in order to have a tight control of their blood glucose levels, as the treatment requires. Repeated lancing in limited surface areas (such as on the fingertip) may result in the formation of calluses. This leads to increased difficulty in drawing blood and increased pain. Moreover, the need to obtain a small blood sample for other home use diagnostic applications (e.g., for cholesterol monitoring) is becoming more commonplace. It, therefore, is desirable to develop a blood sampling method that eliminates the use of needles/lancets and is free of pain or discomfort. It is also desirable to be able to obtain biological fluid samples from other skin sites that are less sensitive than fingers.

For both drug delivery and biological fluid sampling, non-invasive and minimally invasive methods are preferred over invasive methods (e.g., needle injection) since they may easily be self-administered and are pain free. U.S. Pat. Nos. 5,250,028 and 5,843,113, PCT Patent Applications Nos. WO98/11937 and WO97/48440, and Henry et al (*Microfabricated Microneedles: A Novel Approach to Transdermal Drug Delivery*, S. Henry, D. V. McAllister, M. G. Allen and M. R. Prausnitz, Journal of Pharmaceutical Sciences, Vol. 8, August 1998, pages 922-925), disclose perforation or disruption of the skin barrier membrane with mechanical means, e.g., with either small blades or needles, for such purposes. U.S. Pat. Nos. 5,421,816; 5,445,611 and 5,458,140 disclose, as a replacement for invasive sampling, the use of ultrasound to act as a pump for expressing interstitial fluid directly through visually intact (i.e., non-lanced) skin. Other means of treating a tissue to increase transiently the tissue permeability to enhance molecular transport for drug delivery and/or for sampling of interstitial fluids are disclosed in U.S. Pat. Nos. 5,019,034, 5,547,467, 5,667,491, 5,749,847, 5,885,211, and 5,441,490 and PCT Patent Application WO 95/12357.

The object of the present invention is to provide a device and a method using a shear device to perforate the skin barrier for obtaining a sample of a bodily fluid through a membrane and/or deliver an active agent (e.g., for therapeutic purposes). The method disclosed in this invention is needle-less and painless, and is particularly suitable to obtain the biological fluid from less sensitive skin areas other than fingers.

SUMMARY OF THE INVENTION

The present invention features a method for transporting a molecule through a mammalian barrier membrane (e.g., the of skin, buccal, vaginal, and rectal membranes of a mammal such as a human) of at least one layer of cells comprising the steps of: (i) ablating the membrane with a shear device comprising a shear sheet containing at least one opening and a shear member (e.g., a shear blade such as those used in electric razors), where the sheet is contacted with the membrane such that a portion of the membrane is forced through the opening and the shear member (e.g., moving parallel to the shear sheet) ablates the portion of the membrane exposed through the opening; and (ii) utilizing a driving force to move the molecule through the perforated membrane.

In one embodiment, the portion of the membrane is forced into the opening by a pressure force (e.g., mechanical pressure such a pressing the shear sheet against the membrane or suction such as caused by a vacuum).

In one embodiment, the shear device further comprises a driving unit to move the shear member. The driving unit may be the operator of the device manually moving the shear member or an electric motor (e.g., powered by a battery or an AC or DC power cord connecting to an external power supply) moving the shear member.

In one embodiment, the driving force for moving the molecule is selected from a group consisting of iontophoresis, electro-osmosis, reverse iontophoresis, electroporation, phonophoresis, pressure gradients, and concentration gradients. In one embodiment, the molecule is an active agent such as a pharmaceutical (e.g., a polysaccharide, peptide, protein, or polynucleotide) transported through the membrane into the mammal. In one embodiment, the molecule is transported from within the mammal (e.g., a molecule within the interstitial fluid of blood of the mammal) out through the membrane.

In one embodiment, the device further comprises a sensor, the feedback from which that modifies the driving force (e.g., by starting, speeding, slowing, or stopping the shear member's motion to enhance sufficient but not excessive membrane ablation). In one embodiment, the sensor is selected from the group consisting of pressure sensor (e.g., to ensure proper pressure of the device against the skin), conductivity sensor and/or impedance sensor (e.g., to measure the change in conductance or impedance of the barrier membrane), temperature, and pH, or other bio-substance sensor.

Other features and advantages of the present invention will be apparent from the brief description of drawings, the detailed description of the invention and from the claims.

BRIEF DESCRIPTION OF THE DRAWINGS

FIGS. 5a and 5b are respective profiles of blood glucose and plasma insulin concentrations in four pigs following subcutaneous injection of 5 IU of insulin.

FIGS. 6a and 6b are respective profiles of blood glucose and plasma insulin concentrations in two pigs following transdermal insulin delivery by passive diffusion. Shear perforation was performed on the test skin sites prior the insulin delivery.

DETAILED DESCRIPTION OF THE INVENTION

Figure 1:
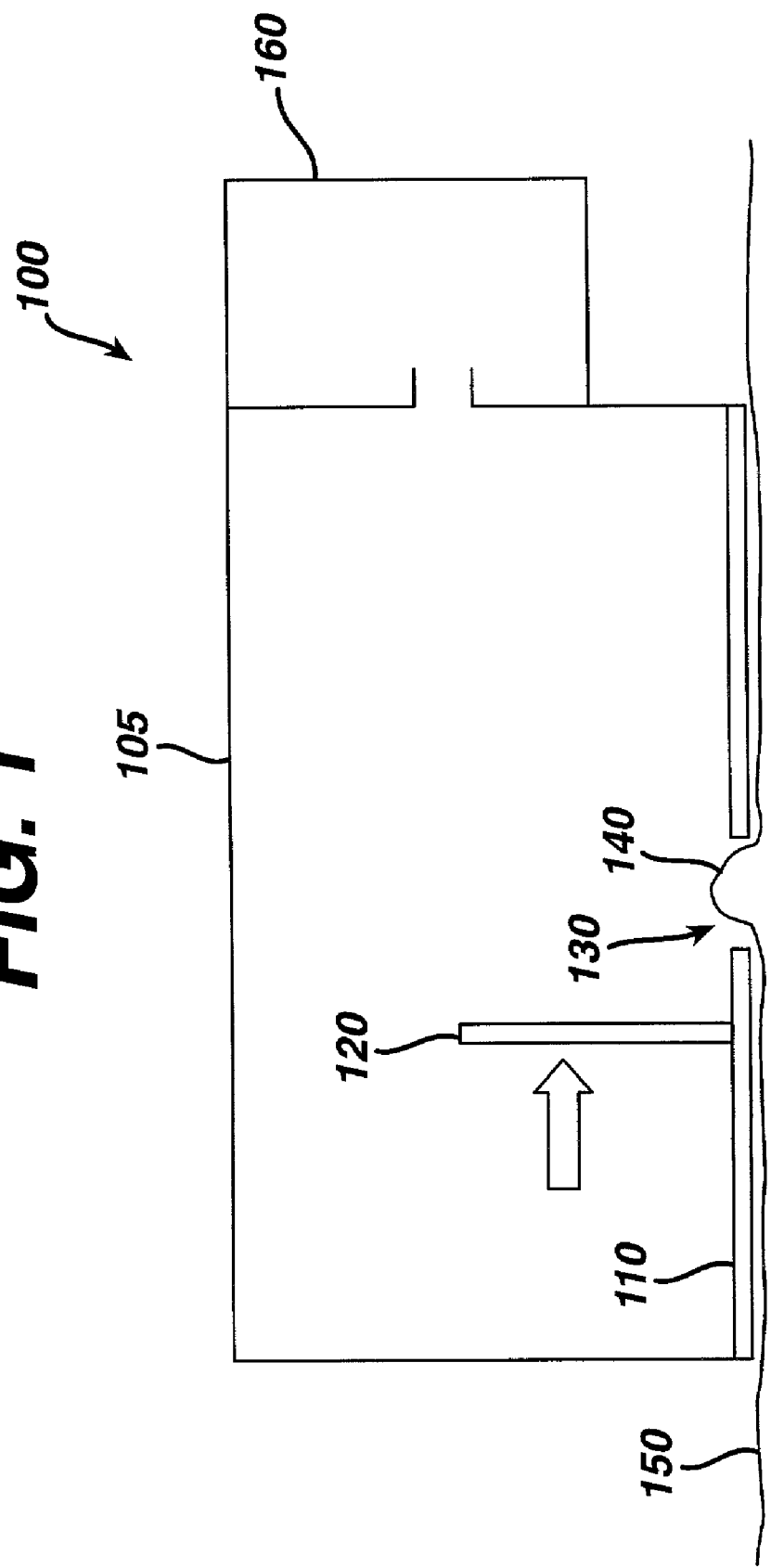
FIG. 1 is a schematic illustration, in cross-section view, of the elements of a shear device of the present invention.

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

In one aspect, the present invention relates to a method whereby it is possible to increase and control the transport of molecules across barrier membranes (e.g., tissues including mammalian skin and mucosal membranes such as rectal, vaginal, and buccal membranes) using a shear force to ablate the membrane in order to enhance transport for the molecules. This method of ablating the barrier membrane (e.g., human skin) is herein termed as "shear perforation." What is meant by ablation is the removal of at least one layer of cells on the membrane. While all of the layers of cells of the membrane do not need to be removed, transport of the molecule is generally enhanced as the more cell layers that are removed. The ablation of the membrane (e.g., the removal of the layer of cells) is a result of the shearing the exposed portion of the membrane through the opening of the shear sheet by the shear member (e.g., the shear blade). As used herein, the term "pore" refers to the area of ablation of the membrane by the shear member leading to an increased molecular transport. In this context, a pore is not restricted by its size and shape, and will often be similar in size and shape to the opening of the shear sheet that it passed through. The shear perforation process may result in an array of such pores.

Because the shear perforation in the present invention destroys the membrane at the point of application, this transport enhancement method is essentially independent of many differences in membrane properties, either between different subjects or on the same subject but on the different anatomic sites. Examples of such differences include the chemical compositions of the membrane (e.g., lipid and ceramide contents), membrane mechanic properties (e.g., elasticity and toughness), and electric properties (e.g., conductivity), as well as biological characteristics (e.g., numbers and types of sweat glands and hair follicles). These differences are known to have a profound impact on transdermal drug delivery.

For example, stratum cornea with different lipid contents may respond differently toward the use of chemical penetration enhancers that primarily affect lipid domain and pathways. Stratum cornea thickness also affects most transdermal delivery relying on passive diffusion of drugs. Mechanical properties, such as skin elasticity and toughness dictate the outcome of mechanical ablation of stratum corneum utilizing methods described in PCT Patent Applications WO 98/11937 and WO 97/48440, U.S. Pat. Nos. 5,250,023 and 5,843,114, and Henry et al., "*Microfabricated Microneedles: A Novel Approach to Transdermal Drug Delivery*", S. Henry, D. V. McAllister, M. G. Allen and M. R. Prausnitz, Journal of Pharmaceutical Sciences, Vol. 8, August 1998, pages 922-925. Since transdermal drug delivery following the shear perforation of the skin eliminate these variables by creating new openings in the stratum corneum as drug transport pathways, this invention provides a superior method for transdermal and transmucosal drug delivery over methods known in the art.

Furthermore, the pores created by the shear perforation method according the present invention are not transient (e.g., in contrast to electroporation), but permanent in a sense these pores will remain open until the new cells re-grow over the opening. This result simplifies the drug delivery process by eliminating the need for constant monitoring the state of the transient microscopic "pores" as in electroporation.

An advantage of the shear perforation method is its ability to increase desired material transport across the barrier membrane which otherwise is rather impermeable. Thus, the present invention further pertains to a process of utilizing a driving force to move molecules across the regions of the membrane undergoing, or having undergone, shear perforation.

Electricity may be employed to move molecules across the perforated barrier membrane by applying an electric potential gradient across the membrane. There are three types of electrically facilitated drug transport through the skin barrier, namely, iontophoresis, electro-osmosis and electroporation. In transdermal iontophoresis, an ionized molecule (e.g., drug ion) migrates into the skin driven by an applied electric potential gradient. In transdermal electro-osmosis, a non-ionic or ionic molecule is carried by a fluid which is driven across the skin by an applied electric potential gradient. When electro-osmosis and/or iontophoresis is used to move non-ionized and/or ionized molecule out of the barrier membrane (e.g., the skin or mucosa) for diagnostic purpose, the procedure is called reverse iontophoresis. Electroporation is the microscopic perforation of the skin barrier by extremely short pulses of high electric voltage and low current. These methods are described in Ying Sun, "Skin Absorption Enhancement by Physical Means: Heat, Ultrasound, and Electricity", *Transdermal and Topical Drug Delivery Systems*, Interpharm Press, Inc., 1997, pages 327-355.

Thus, an electric force, in a form of iontophoresis, electroporation, electro-osmosis, or reverse iontophoresis, can be used as the driving force to transport molecules across the tissue once the pores have been formed through shear perforation. For example, following the completion of shear perforation, an electrical potential of low voltage (e.g., about or less than 9 volts) and current density (e.g., about or less than 0.4 mA/cm$^2$) for iontophoresis is applied to the shear perforated skin site. Ionic species present in this low voltage field will migrate toward sources of opposite polarity. Thus, if an electrode of opposite polarity is present at another distant skin site, charged drug ions will migrate through the pores created by shear perforation into the body. Neutral molecules can also be moved by electro-osmosis for transdermal delivery or by reverse iontophoresis for interstitial fluid sampling.

A single apparatus in the present invention may have the build-in capability to operate several functions simultaneous or in sequence. Taking gene delivery to dermal tissue as an example, a three-step process may be conducted: (1) using the shear perforation to create an array of small pores on stratum corneum, (2) using passive diffusion or applying iontophoresis to transport the genes across the stratum corneum into living epidermis and dermis tissues, and (3), applying electroporation to increase gene uptake into the epidermis and dermis cells by increasing cell membrane permeability. U.S. Pat. Nos. 5,019,034, 5,547,467, 5,667,491, and 5,749,847 and PCT Patent Application WO 99/22809 describe the use of electroporation to increase tissue permeability. Iontophoresis and electroporation in the steps (2) and/or (3) may also be replaced by phonophoresis (i.e., the use of ultrasound for enhancing material transport).

In one embodiment, the driving force may be of acoustic energy in nature, such as in the case when ultrasound (i.e., frequencies above 20 kHz) or an audible sound (i.e., frequencies below 20 kHz) is used to enhance drug delivery (a process called "phonophoresis"). The use of phonophoresis is described in Ying Sun, "Skin Absorption Enhancement by Physical Means: Heat, Ultrasound, and Electricity", *Transdermal and Topical Drug Delivery Systems*, Interpharm Press, Inc., 1997, pages 327-355.

The driving force may also be other physical or chemical force such as provided by a temperature gradient, a pressure gradient, or simply a concentration gradient (e.g., a concentrated form of the material to be transported is held in a reservoir contacting the tissue surface at the site of shear perforation). The transdermal delivery patches commercially available now for certain systemic treatment drugs (e.g., nitroglycerin, nicotine, fentanyl, scopolamine) are all based on the drug concentration gradient as driving force, i.e., depending on the passive diffusion of drug molecules across the skin barrier. With respect to the use of a concentration gradient of the molecules to be transported, the driving force of concentration gradient may be combined with an externally elevated hydrostatic pressure to facilitate the molecules to pass through the pores into the underlying tissue.

The shear perforation transport processes associated with this invention lend themselves to use with a wide variety of molecules including drugs and molecules of diagnostic interest. Molecules (e.g., active agents) which may be delivered by the method and/or device of the present invention include, but are not limited to, any material capable of exerting a biological effect on a human body, such as therapeutic drugs, including, but not limited to, organic and macromolecular compounds such as polypeptides, proteins, polysaccharides, and nucleic acid materials comprising DNA; and nutrients.

Examples of polysaccharide, polypeptide and protein active agents include, but are not limited to, heparin and fragmented (low molecular weight) heparin (e.g., dalteparin sodium), thyrotropin-releasing hormone (TRH), vasopressin, gonadotropin-releasing hormone (GnRH or LHRH), melanotropin-stimulating hormone (MSH), calcitonin, growth hormone releasing factor (GRF), insulin, erythropoietin (EPO) and its analogs, interferons (e.g., interferons alpha & beta), monoclonal antibody (e.g., infliximab, abciximab. edrecolomab), retaplase, oxytocin, captopril, bradykinin, atriopeptin, cholecystokinin, endorphins, nerve growth factor, melanocyte inhibitor-I, gastrin antagonist, somatotatin, encephalins, and cyclosporin and their derivatives (e.g., biologically active fragments or analogs). The active agents include anesthetics, analgesics, drugs for psychiatric disorders, epilepsies, migraine, stopping drug additions and buses; anti-inflammatory agents, drugs to treat hypertension, cardiovascular diseases, gastric acidity and GI ulcers; drugs for hormone replacement therapies and contraceptives; antibiotics and other antimicrobial agents; antineoplastic agents, immunosuppressive agents and immunostimulants; and drugs acting on blood and the blood forming organs including hematopoietic agents and anticoagulants, thrombolytics, and antiplatelet drugs.

Other active agents that can be delivered into the body using the shear device in the present invention include vaccines for various diseases, such as those for influenza, AIDS, hepatitis, measles, mumps, rubella, rabies, rubella, avercella, tetanus, hypogammaglobulinemia, Rh disease, diphtheria, botulism, snakebite, back widow bite and other insect bite/sting, idiopathic thrombocytopenic purpura (ITP), chronic lymphocytic leukemia, cytomegalovirus (CMV) infection, acute renal rejection, oral polio, tuberculosis, pertussis, Haemophilus b, Pneumococcus, and *Staphylococcus aureus*. See, e.g., R. Ulrich, et al in Vaccine, Vol. 16, No. 19, pages 1857-1864, 1998. An example of a vaccine against staphylococcus intoxication is described in PCT Patent Application WO 00/02523. Other active agents suitable for transdermal delivery to treat allergies are selected from the group consisting of fine particles or extracts from natural substances (e.g., from herbs, grass seeds, pollens, and animal debris).

Cationic and anionic active agents, such as those described in M. Roberts, et al., "Solute Structure as a Determinant of Iontophoretic Transport", *Mechanisms of Transdermal Drug Delivery*, R. O. Potts and R. H. Guy, Ed., Marcel Dekker, pages 291-349, 1997, may be delivered with a device utilizing iontophoresis. Active agents that are non-ionized or with a net charge equal to zero may also be delivered with this apparatus by electro-osmosis as described by Pikal in "The role of Electroosmotic Flow in Transdermal Iontophoresis", Advanced Drug Delivery Reviews, pages 210-238, Vol. 9, 1992.

Similarly, molecules and substances of diagnostic interest, including both naturally occurring substances and therapeutically introduced molecules in interstitial fluid, can be extracted out of the barrier membrane by electro-osmosis or reverse iontophoresis for subsequent assaying. These molecules and substances include, but are not limited to, natural and therapeutically introduced metabolites, hormones, amino acids, peptides and proteins, polynucleotides, cells, electrolytes, metal ions, suspected drugs of abuse, enzymes, tranquilizers, anesthetics, analgesics, anti-inflammatory agents, immunosuppressants, antimicrobials, muscle relaxants, sedatives, antipsychotic agents, antidepressants, antianxiety agents, small drug molecules, and the like. Non-limiting representative examples of such materials include glucose, cholesterol, high density lipoproteins, low density lipoproteins, triglycerides, diglycerides, monoglycerides, bone alkaline phosphoatase (BAP), prostate-Specific-Antigen (PSA), antigens, lactic acid, pyruvic acid, alcohols, fatty acids, glycols, thyroxine, estrogen, testosterone, progesterone, theobromine, galactose, uric acid, alpha amylase, choline, L-lysine, sodium, potassium, copper, iron, magnesium, calcium, zinc, citrate, morphine, morphine sulfate, heroin, insulin, interferons, erytheopoietin, fentanyl, cisapride, risperidone, infliximab, heparin, steroids, neomycin, nitrofurazone, betamethasone, clonidine, acetic acid, alkaloids, acetaminophen, and amino acids. More than one substance can be sampled at one time.

In one embodiment, the invention includes continuous monitoring of the levels of glucose or glucose metabolite (e.g., lactic acid) from the bodily fluids, such as blood and interstitial fluid. The method can also be used for measurement of blood substance (e.g. glucose) levels in either a semi-continuous or a single measurement method. The method can be practiced by a device that provides electrodes or other means for applying electric current to the tissue at the collection site; one or more collection reservoirs or sampling chambers to receive the substance (glucose); and a substance concentration measurement system. U.S. Pat. Nos. 5,735,273, 5,827,183, and 5,771,890 describe methods of reverse iontophoresis for non-invasive interstitial fluid sampling for diagnostic purpose. However, the methods of extracting interstitial fluid from intact skin with reverse iontophoresis as described in these U.S. patents have a low extraction efficiency and, therefore, suffer from low glucose signal, high measurement noise, low accuracy and require long equilibrium time. In contrast, the use of reverse iontophoresis to extract interstitial fluid from the shear-perforated skin as described in the present invention, can result in a much higher outward interstitial fluid flow rate, leading to an improved accuracy and shortened equilibrium time.

Interstitial fluid may also be extracted from the opening(s) created by shear perforation on the barrier membrane (e.g., using one of the following methods: a mechanical suction device with the structure similar to a syringe; a manual mechanical suction device using a piston and a series of one-way valves with the working mechanism similar to commercial apparatuses such as MityVac II® vacuum pump (Prism Enterprises, San Antonio, Tex., USA) and Aspivenin® (ASPIR, Sannois, France); a small size motor-driving suction/vacuum pump; a rubber pipeting suction bulb (e.g., Bel-Bulb® Pipettor, Bel-Art Products, Inc., NJ, USA; Welch® Suction Cup Electrode, Hewlett Packard, Rockville, Md., USA); and a pre-manufactured vacuum chamber with the working mechanism similar to the Vacumtainer® (Becton, Dickinson and Company, Franklin Lakes, N.J.). To enable a speedy extraction of interstitial fluid with minimal discomfort when a mechanical suction device is used. In one embodiment, the suction force is within the range of 5 to 75 cm Hg (e.g., 20 to 60 cm Hg). Alternative methods of extracting interstitial fluid include placing on the opening(s) a capillary tube, or an absorbent material (e.g., gauze or nonwoven pad, sponge, hydrophilic polymers of porous structure); or combining aforementioned methods. For example, interstitial fluid can be extracted out of the pores of perforated skin following shear perforation using either a vacuum or an osmotic pressure by contacting the perforated skin with a hygroscopic material such as glycerin, urea, polyvinylidone polymer either alone or as a concentrate aqueous solution. The glucose and other biological substances of interest in the extracted interstitial fluid can be analyzed by the methods described in D. Buerk, Biosensors—Theory and Applications (Technomic Publishing Company, Inc., 1993), and in the U.S. Pat. Nos. 5,789,255, 5,453,360, 5,563,031, 5,304,468, 5,563,042, and 5,843692.

After the interstitial fluid is driven out of the barrier membrane (e.g., the skin) through the opening(s) created by the shear perforation process by one or more aforementioned driving forces, analysis of certain biological substances in the interstitial fluid can be performed with an analytical method such as a sensor based on enzymatic reaction, antibody interaction, ion-selective electrode, oxidation-reduction electrode; infrared (IR), ultraviolet (UV) spectrophotometry, or colorimetry.

Thus, in one aspect, the invention features an apparatus for performing the shear perforation method of the present invention. One embodiment of a shear device for producing the pores in a barrier membrane via shear perforation for the purpose of drug delivery is illustrated schematically in FIG. 1. In FIG. 1, the apparatus, represented generally as 100, comprises a housing 105 which houses a power unit (e.g., batteries), an electric motor, and mechanical apparatus (not shown) to drive the shear blade 120 to move over the shear sheet 110 in a reciprocating or circulating motion. The materials and construction of the shear device 100 are similar to commercially available screen/foil shavers used for facial and body shaving (e.g., Remington Microscreen®, Remminton, Bridgeport, Conn., USA; Braun Pocket Twist Plus®, Braun, Kronberg, Germany; National ES815®, Matsushita Electri Works Ltd., Japan, and Huling® Battery Shaver, Ban Doa Ltd., Shanghai, China), and those described in U.S. Pat. Nos. 3,949,469, 4,009,518, 3,742,603, 4,035,914, 4,837,929, 5,261,161, 4,606,121, 4,115,920, 5,185,926, 4,991,295, 5,473,818, 4,184,250, 3,756,105, and D0307,645.

Although only one opening 130 and one shear blade 120 are shown in FIG. 1, the device may comprise a plurality of such openings and blades. In one embodiment, the shear sheet of the shear perforation device comprises a plurality of the openings (e.g., between 1 and 1000 openings per square centimeter of the shear sheet surface) and a plurality of the blades (e.g., between 1 and 10 blades per square centimeter of the shear sheet surface). The shear sheet 110 may be of varying size (e.g., depending upon the membrane area to be treated or amount active agent of biological fluid to be transported) and varying shape (e.g., flat or with a curvature such as a convex curvature). The blade edge may also be of any shape and, preferably, should be in a close and smooth contact with the shear sheet 110 during the shear perforation process. The shear blade edge, thus, should have a shape similar to that the shear sheet in contact. For example, if the shear sheet is a curved sheet, the edge of the blade should also be curved in the same curvature, thus enabling a close contact between the shear sheet and blade during reciprocating shear motion of the shear blade.

In operation, the shear device 100 is pressed firmly against human skin 150, so that the skin under the opening 130 is forced into the opening 130 as shown in FIG. 1. As the shear blade 120 glides over the opening 130, it ablates the exposed portion of skin 140 through the opening 130, thus perforating the skin. In one embodiment, the shear blade moves in either a reciprocating motion (e.g., as Remington Microscreen 1® Shaver) or a circular motion (e.g., Huling® Battery Shaver). The depth of ablation (e.g., the number of cell layers removed or destroyed) depends primarily on how much skin is exposed through the opening 130, which in turn depends on the size and shape of the opening 130, and the thickness of the shear sheet 110. Skin shear perforation of the present invention can ablate the stratum corneum, epidermis, and the superficial portion of the dermis. Depending on the size of molecules to be transported and transport rate, the depth of ablation can be controlled to perforate only the stratum corneum, or the stratum corneum and living epidermis, or the stratum corneum, living epidermis, and the superficial portion of the dermis.

A proper skin exposure through the opening 130 can also be achieved by the use of a suction/vacuum device 160 (FIG. 1). By controlling the degree of the suction, a precise amount of the skin can be drawn into the opening 130, and subsequently, be ablated off by the shear blade 120. The suction device can be a manual mechanical suction device using a piston and a series of one-way valves with the working mechanism similar to commercial apparatuses such as Mity-Vac II® vacuum pump (Prism Enterprises, San Antonio, Tex., USA) and Aspivenin® (ASPIR, Sannois, France), a small size motor-driving suction/vacuum pump, or simply a rubber pipeting suction bulb such as Bel-Bulb® Pipettor (Bel-Art Products, Inc., Pequannock, N.J., USA).

The pores created by shear perforation serves as the transport pathway for molecules of interest, such as an active agent (e.g., a pharmaceutical drug) for therapeutic treatment or interstitial fluid for diagnostic sampling. In the case of pore formation for sampling interstitial fluid, there can be a slightly deeper tissue ablation to the underlying living tissues (e.g., up to the superficial dermis), so that more interstitial fluid or even blood can be collected through the pores.

In one embodiment, the shear device comprises a conductivity sensor for measuring the electrical resistance or impedance of the barrier membrane. Because intact barrier membrane (e.g., the skin) has a higher electric resistance than that of the ablated membrane, the change in the membrane conductance or impedance detected by the conductivity sensor during perforation process provides a signal to the control unit to activate and/or to deactivate the shear device, e.g., incorporation of the conductivity sensor into the shear device deactivates the shear blade action once the membrane is ablated, thereby preventing the excess ablation and unnecessary deeper tissue injury. Examples of electrical circuits of such conductivity sensors to activate and deactivate the motor of the shear device are set forth below in Examples 5 and 6. In one embodiment of the device would determine absolute impedance or conductance at the tissue surface to insure safety and prevent cutting of a previously ablated area.

The impedance or conductance based electrode could serve a dual purpose and function as a delivery electrode utilizing delivery means such as iontophoresis to enhance delivery. The entire circuit whether analog or microprocessor based could be contained in a drug delivery patch which monitors the skin during the tissue ablation process to insure breakdown of the stratum corneum and then provides a driving force using iontophoresis, electroporation, or concentration gradients to facilitate drug delivery.

The shear device may contain a microprocessor control for additional flexibility and improved feedback control. The microprocessor-based device could communicate information about the device settings, cutting speed, procedure duration, and effectiveness through serial, optical, or telemetry based methods. Example of such a device is set forth in Example 6.

In one embodiment, the shear device contains infrared sensors to monitor tissue effects at the surface of the skin such as erythema and/or conduct spectroscopy of specific analytes at the skin surface such as glucose. In one embodiment, the shear device contains a pressure, optical, and/or mechanical sensors to measure compression forces of the cutting mechanism against the skin.

In one embodiment, the metal shear sheet 110 and/or shear blade 120 can serve as a conductivity probe. With a second conductivity probe and a conductance measurement circuit (not shown), a conductivity sensor is formed to monitor electrical resistance or impedance through the membrane 150 (i.e., the skin). U.S. Pat. No. 5,738,107 describes a method for impedance measurement and an electric circuit that can be used in this invention. Other impedance measurement circuits commonly used in biomedical devices are also suitable for this purpose.

In one embodiment, the shear device 100 comprises a pressure sensor for measuring the pressure exerted on the membrane by the sheer sheet. The information obtained by the pressure sensor is used to activate and/or to deactivate the shear blade through a control unit, thereby providing consistent shear perforation of the membrane and minimizing tissue injury.

In another embodiment, the shear device 100 further comprises a mechanic apparatus that is capable generating either a positive or negative pressure (i.e., suction) over the perforated barrier membrane. The positive pressure is used to drive active agents into the membrane, whereas the negative pressure is used to extract bodily fluids (e.g., interstitial fluid or blood) out of the membrane. For diagnostic purposes, interstitial fluid or blood can be collected from the mammal through the pores using means comprising negative pressure (e.g., using suction, as in "Fluorescein Kinetics in Interstitial Fluid Harvested from Diabetic Skin during Fluorescein Angiography: Implications for Glucose Monitoring" by Smith, A. et. Al., *Diabetes Technology & Therapeutics*, Vol. 1, No. 1., pages 21-27, 1999), positive pressure (e.g., mechanical squeezing by the user), and/or electric force (e.g., reverse-iontophoresis, as described in U.S. Pat. No. 5,771,890).

Figure 2A:
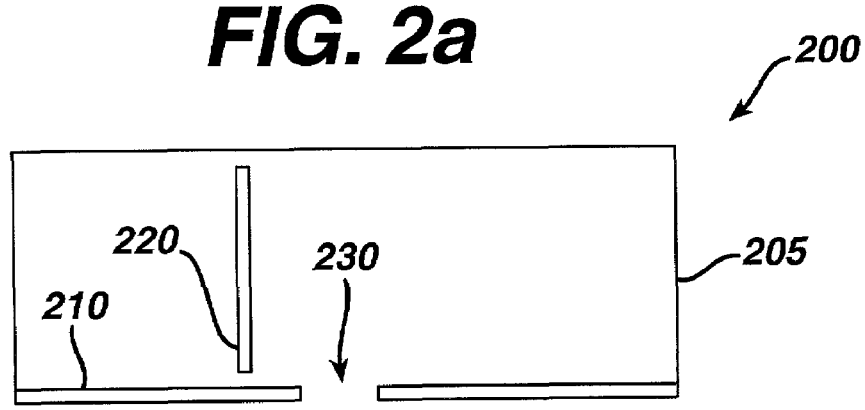
FIGS. 2a, 2b, and 2c are a schematic representation, in cross-section view, of three examples of shear devices of the present invention having different sheer blade shapes.
Figure 2B:
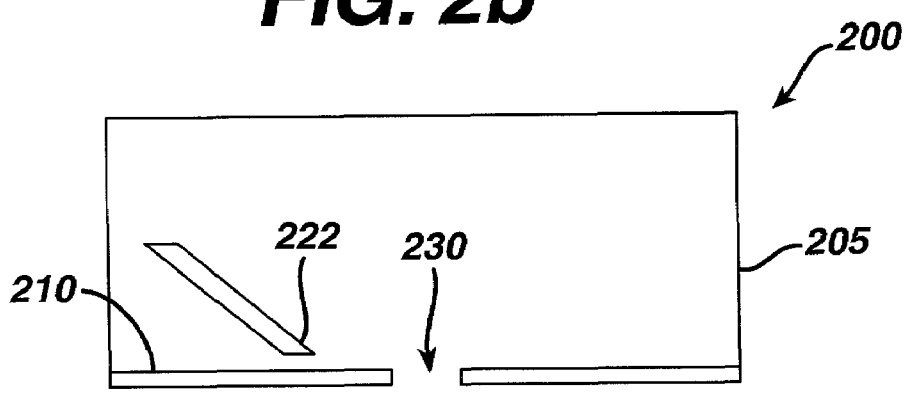
Figure 2C:
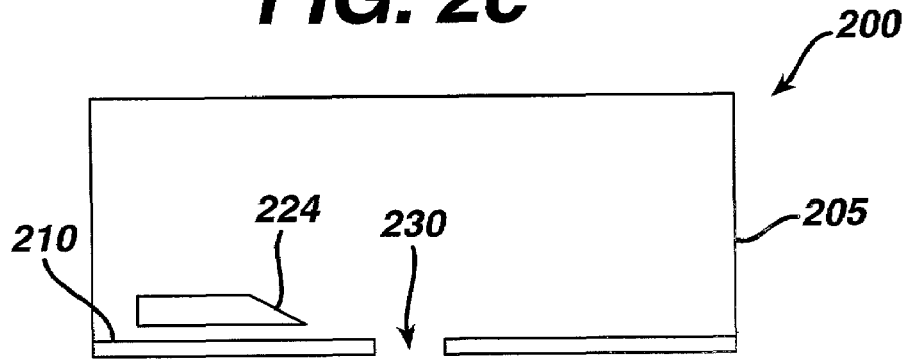
Figure 3A:
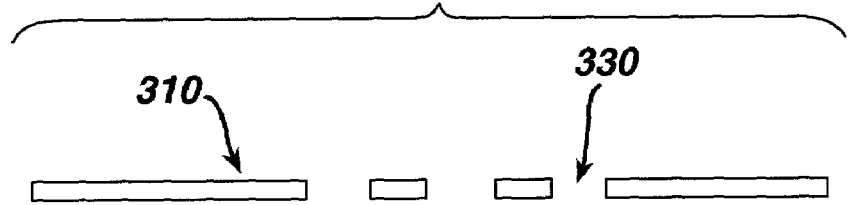
FIGS. 3a, 3b, 3c, and 3d are a schematic representation, in cross-section view, of four examples of the shapes at shear sheet openings that can be used in the sheer device of the present invention.
Figure 3B:
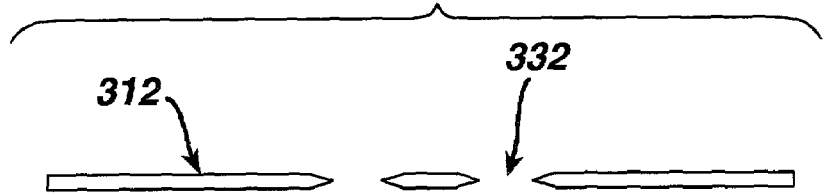
Figure 3C:
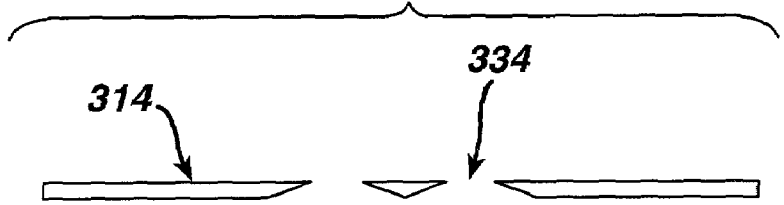
Figure 3D:
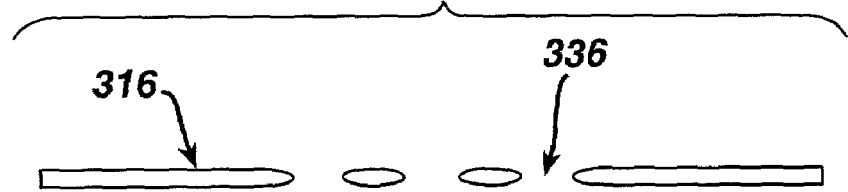

Another embodiment of an apparatus of the present invention, represented generally in FIG. 2 as 200 having housing 205, contains shear sheet 210, opening 230 and three non-restricting examples of differently shaped shear blades 220, 222, and 224 in FIGS. 2a-2c for shear perforation. The shear blades in FIG. 2 can be any thickness, shape, and angle in relative to the shear sheet. In addition, the shear member is not restricted to blades only. In another embodiment, the shear member is an objective with a rough surface on the side in contact with the shear sheet. As the rough-surfaced shear member moves in reciprocating motion or circular motion, the skin exposed through the opening 130 (FIG. 1) is ablated.

Various embodiments of the openings 330, 332, 334, and 336 on the respective shear sheet 310, 320, 330, and 340 of the present invention are shown in FIGS. 3a-3d in cross-section view. As shown in these figures, each shear sheet contains multiple shear openings. The figures show some non-restricting examples of possible inner edges of the openings 330, 332, 334, and 336 on the shear sheet.

Figure 4A:
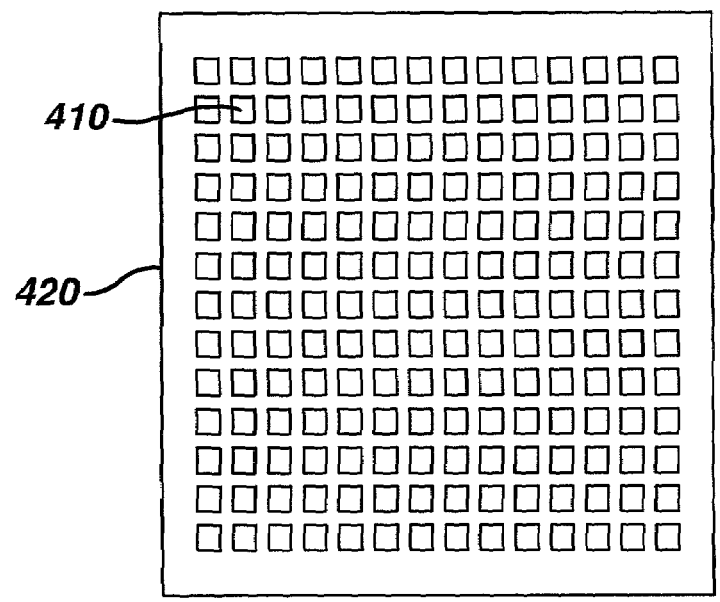
FIGS. 4a and 4b are schematic representations, in top view, of two examples of the shapes of shear sheet openings that can be used in the sheer device of the present invention.
Figure 4B:
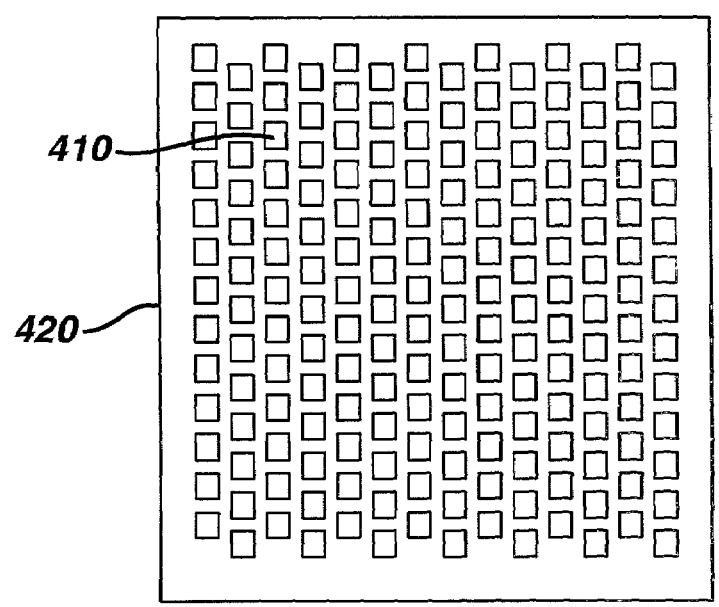

Another embodiment of the arrangement of the openings on the shear sheet of the present invention is shown in FIGS. 4a and 4b in top view. The arrangement of the openings and the shape of the openings on the shear sheet may vary depending on the size, amount, and spacing of the ablation areas (e.g., pores). Examples of the opening shapes include, but are not limited to, round, oval, square, rectangular, triangle, any polygons, narrow slit, and combinations thereof. In one embodiment, the area of each opening is about 0.001 to 5 mm$^2$. The relative ratio of the total opening areas 410 to the space between adjacent openings on a shear sheet 420 can vary significantly depending on a particular need (e.g., within the range of 1:4 and 4:1).

The material used to make the shear sheet shall be strong enough to cause folding of the barrier membrane (e.g., the skin) into the opening 130 (FIG. 1) and subsequent membrane ablation during the shearing process. The material to make the shear blade should be strong enough to ablate the barrier membrane. Examples of such materials for the shear sheet and the shear blade include pure metal, metal alloy, coated metal, ceramic, glassy material, plastics, polymer, or other hard materials such as composites (e.g., metal-polymer, metal-glass, and metal-ceramic) suitable for making the shear sheet and blade, e.g., those materials currently used in commercial shavers for facial and body hair, such as stainless steel, platinum-coated steel, and ruthenium-enriched steel.

In another embodiment of the invention, the shear sheet and shear blade can be part of a detachable and/or disposable unit of the shear device to eliminate potential contamination in repeated applications (e.g., the shear sheet and shear blade can be replaced following each use). The suction unit for facilitating aforementioned shear perforation, or subsequent extracting of bodily fluids, can either be built into the shear device as an integrated device, or as a separate device (e.g., a suction device similar to Aspivenin® manufactured by ASPIR and MityVac II® vacuum pump manufactured by Prism Enterprises, San Antonio, Tex., USA).

In another embodiment of the invention, a further step is used to maintain the micropore pathways by retarding the closure of the pores (i.e., to keep the pores open under occlusion for drug delivery or interstitial fluid sampling). In one embodiment, the pores are kept in contact with a preparation (e.g., a solution, gel, emulsion, suspension, cream, lotion) in an occlusive or semi-occlusive drug delivery patch, which contains active agents to be delivered, as well as the pore-closure-retarding compounds that retard epidermal cell proliferation and/or differentiation or the tissue growth leading to the closure of the pores. Examples of such pore-closure-retarding compounds include, but are not limited to, saccharides, polyssacharides, cyclodextrins, heparin and fragmented (low molecular weight) heparin derivatives, retinoids (e.g., retinoic acid, retinol, and their derivatives), and corticosteroids (e.g., hydrocortisone). Alternatively, the preparation (i.e., solution, gel, emulsion, cream, lotion, etc.) containing the pore-closure-retarding compounds, with or without the active agents, can be applied topically, i.e., directly to the perforated skin area in a way similar to the application of a skin moisturizing cream.

To evaluate the feasibility of using shear perforation as a permeability enhancing method to increase transport across a barrier membrane such as the skin, several shear perforation experiments were conducted to examine molecular transport of bodily fluids and a protein drug through human and pig skin in vivo.

EXAMPLE 1

Extraction of Interstitial Fluid (ISF) from Human Skin Following Shear Perforation Shear perforation of human skin was performed on the ventral leg (calf) of one male volunteer using a commercially available shaver for facial hairs (National Battery-operated Shaver, ES815B, Mastushita Electric Works, Ltd, Japan). The screen of the shaver was covered with a metallic tape (Ideal Tape Co., Lowell, Mass., USA), so that only 1 cm² square area at the center of the screen was exposed. The shaver was pressed firmly on the skin for about 5 seconds. Neither pain nor discomfort was experienced by the volunteer. The perforation skin site (0.7 cm²) showed only slight erythema after the skin perforation procedure. A hand-held suction device (MityVac II vacuum pump, Prism Enterprises, San Antonio, Tex., USA) was applied to the perforation skin site with about 70 cm Hg of suction for a certain time duration. Interstitial fluid (a clear, slightly yellowish liquid) extracted out the pores from shear perforation was collected using an absorbent paper, and quantified by weighing. The procedure was repeated immediately for several times on the same skin perforation site with suction duration ranging from 1 to 4 minutes. The results are tabulated in TABLE 1.

TABLE 1

| Suction Number | Suction Duration (Minutes) | Interstitial Fluid Extracted after Each Suction (mg) | Interstitial Fluid Extracted per Minute (mg/minute) |
| --- | --- | --- | --- |
| 1 | 1 | 4.2 | 4.2 |
| 2 | 2 | 11.0 | 5.5 |
| 3 | 3 | 16.1 | 5.4 |
| 4 | 4 | 13.6 | 3.4 |

A second experiment of shear perforation and suction ISF extraction was conducted with modified procedures. Shear perforation of human skin was performed on the ventral forearm skin of one male volunteer using a shaver (National Battery-operated Shaver, ES815B, Mastushita Electric Works, Ltd, Japan). The same procedures were performed on three adjacent skin sites about 1 inch apart in order to obtain an average ISF value (i.e., n=3). The screen of the shaver was covered with a metallic tape (Ideal Tape Co., Lowell, Mass., USA), so that only 1 cm² square area at the center of the screen was exposed. The shave was pressed firmly on the skin for about 2 seconds. No pain nor discomfort was experienced by the volunteer. The perforation skin site (0.7 cm²) showed only slight erythema after the skin perforation procedure. A hand-held suction device (Aspivenin®, ASPIR, Sannois, France) was applied to the perforation skin site with about 40-50cm Hg vacuum for 1 minute. Interstitial fluid was collected using an absorbent paper, and quantified by weighing. The procedure was repeated for 4 times with certain time period (from 2.5 to 4 hours) separating each suction ISF extraction on the same skin site during the day. The suction ISF extraction procedures were continued for two more days on the same skit sites. The timings of all the suctions and ISF results were shown in TABLE 2.

TABLE 2

| Suction Number on a Given Day | Time of the Day | Site 1 INF Wt (mg) | Site 2 INF Wt (mg) | Site 3 INF Wt (mg) | Average ISF Wt (mg) | Standard Deviation |
| --- | --- | --- | --- | --- | --- | --- |
| Day 1 No. 1 | 9:30 AM | 3.6 | 2.9 | 3 | 3.2 | 0.4 |
| Day 1 No. 2 | 12:30 PM | 4.2 | 2.8 | 4 | 3.7 | 0.8 |
| Day 1 No. 3 | 3:00 PM | 6.5 | 6.4 | 8.7 | 7.2 | 1.3 |
| Day 1 No. 4 | 5:30 PM | 12.7 | 7.6 | 9.2 | 9.8 | 2.6 |
| Day 2 No. 1 | 8:30 AM | 7.4 | 6 | 8.4 | 7.3 | 1.2 |
| Day 2 No. 2 | 12:30 PM | 5.4 | 3.3 | 7.1 | 5.3 | 1.9 |
| Day 2 No. 3 | 3:00 PM | 3.5 | 1.4 | 5.7 | 3.5 | 2.2 |
| Day 2 No. 4 | 5:30 PM | 3 | 4.1 | 6.2 | 4.4 | 1.6 |
| Day 3 No. 1 | 8:30 AM | 4.1 | 4.8 | 7.9 | 5.6 | 2.0 |
| Day 3 No. 2 | 12:30 PM | 3.1 | 3.4 | 6.9 | 4.5 | 2.1 |
| Day 3 No. 3 | 3:00 PM | 4.1 | 4.4 | 8.3 | 5.6 | 2.3 |
| Day 3 No. 4 | 5:30 PM | 4.9 | 4.7 | 7.4 | 5.7 | 1.5 |

The results in TABLE 1 and TABLE 2 show that interstitial fluid could be extracted from shear-perforated skin of a human for subsequent analysis of its contents.

For those diabetic patients who are under intensive insulin therapy and require glucose monitoring at least four times per day (N. Engl. J. Med., Vol. 342, Pages 381-389, 2000), this painless method provides a practical means to replace the painful finger pricking method currently in use for glucose monitoring. Furthermore, this result also demonstrates the feasibility of developing a fully automated, small and wearable glucose monitoring device, which periodically applies a suction to a shear perforated skin site to obtain small quantity of interstitial fluid for glucose analysis. The time intervals between two glucose checks can be set either very close or rather apart by a physician or the patient according to the individual need, thus achieving frequent or near-continuous glucose monitoring. The pain-free and minimal invasive nature of the shear-perforation and suction ISF extraction described in the present invention also makes it an ideal sampling technique for home-monitoring kits of many other biological chemicals/markers of interest,

EXAMPLE 2

Subcutaneous Injection of Insulin as a Control Experiment for Transdermal Insulin Delivery The subcutaneous administration of insulin provides a dose response to which a comparative measure of transdermally delivered insulin can be made. An insulin dose of 5 IU insulin (Regular Iletin® II, Insulin Injection, USP, Purified Pork, Eli Lilly and Company, Indianapolis, Ind., USA) was subcutaneously injected in the rear mid-ventral area of each of four female Yorkshire pigs (weight: 22-26 kg) with a 1 cc Sub-Q Precision Glide® Needle (Becton-Dickinson and Company, Franklin Lakes, N.J., USA). FIG. 5a shows that subcutaneous insulin administration resulted in the expected rapid reduction in blood glucose concentration.

Figure 5B:
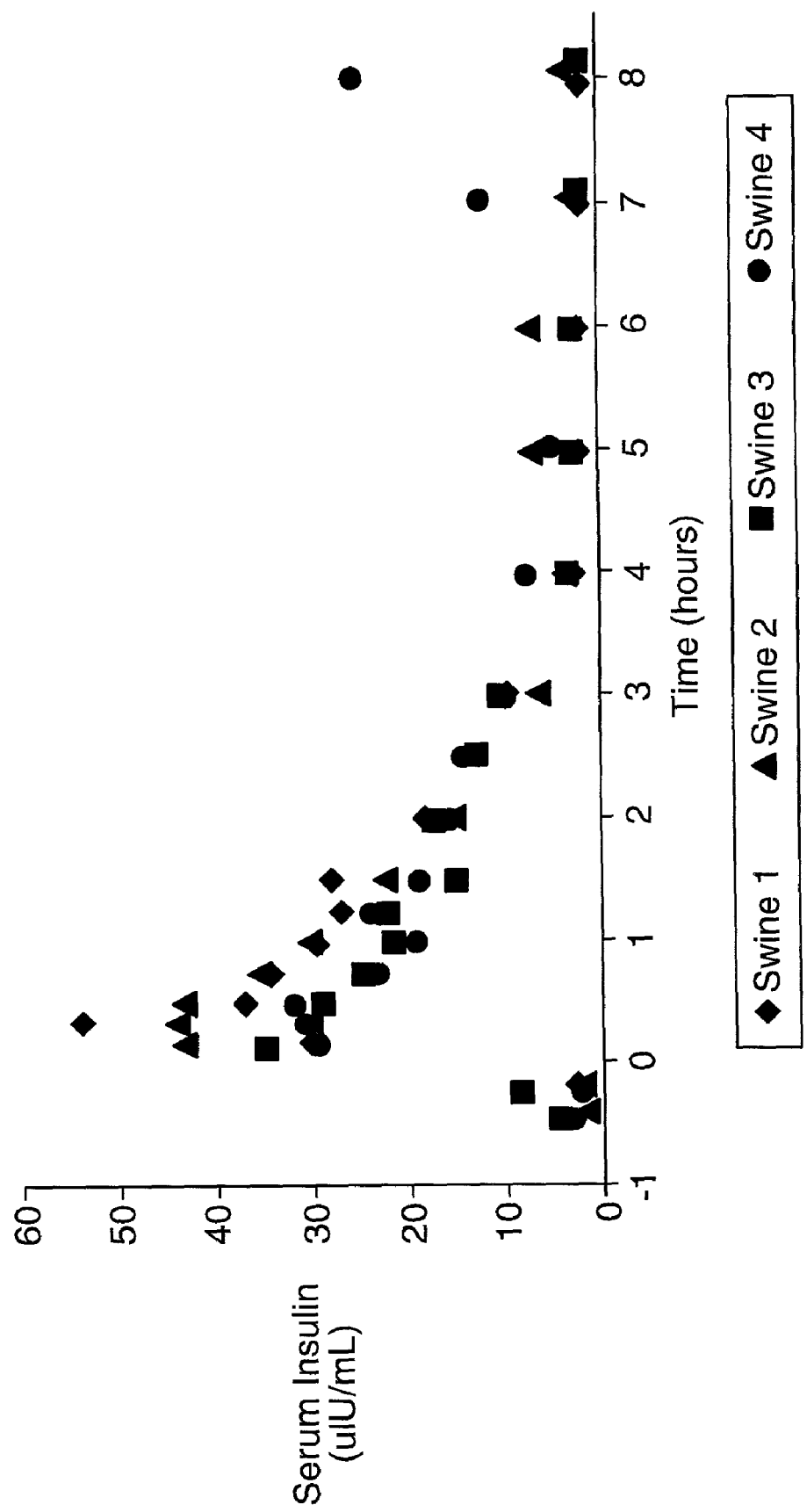

FIG. 5b shows that a 5 IU insulin subcutaneous injection resulted in a peak insulin concentrations of 31-55 µIU/ml. As the insulin concentrations went back to its basal concentration (FIG. 5b), the blood glucose concentrations also were gradually returned toward its pre-insulin injection level (FIG. 5a).

EXAMPLE 3

Transdermal Delivery of Insulin into Swine Following Shear Perforation of the Skin The stratum corneum is recognized as the primary barrier to percutaneous absorption of drug applied to the skin surface. The densely structured outmost skin layer consisting of flattened and keratinized dead skin cells provides a formidable permeation barrier to most small and virtually all large compounds. It is well known in the field of transdermal drug delivery that a protein drug such as insulin cannot penetrate into the intact skin of human and swine. Our own experiment confirmed this (result not shown). This example investigates in vivo transdermal delivery of insulin into swine following application of shear perforation to remove the stratum corneum barrier at the test site.

Two female Yorkshire pigs of the same body weight range as those in Example 2 were immobilized with anesthetics. The test site on the side of the chest was prepared by clipping lightly off the hair and cleaning with an alcohol wipe. Special care was taken not to damage the skin. Shear perforation of the pig skin was performed with a Remington shaver (Remington Microscreen 1®, Remington, Bridgeport, Conn., USA) by pressing its screen firmly on the skin for about 1 second. This procedure was repeated at an adjacent skin site until 10 $cm^2$ of the skin was shear-perforated. Only slight erythema was observed on the test site. A drug reservoir patch made of silicone rubber (Silastic® Sheet, Medical Grade, Dow Corning Corp., Midland, Mich., USA) was affixed to the test skin with silicone adhesive (Secure® Adhesive, BT-401, Factor II, Inc., Lakeside, Ariz., USA). The silicone patch had a 0.5 ml drug reservoir, which communicated with the perforated skin through a 10 $cm^2$ opening. The thickness of the drug reservoir was 0.5 mm. An insulin solution (0.5 ml, Regular Iletin® II, Insulin Injection, USP, Purified Pork, Eli Lilly and Company, Indianapolis, Ind., USA) was placed into the drug reservoir which covered the shear-perforated skin to allow insulin molecules to enter the pig body through the pores on the stratum corneum driven by insulin concentration gradient. Transdermal insulin delivery was conducted in this way for 50 minutes. Insulin delivery was then terminated by removing the insulin patch. Blood samples were taken from the pigs prior to, during, and after transdermal insulin delivery for determination of blood glucose and insulin concentrations.

FIG. 6a shows the blood glucose profiles from this study. Drastic reduction in the blood glucose of the test pigs after initiation of transdermal insulin delivery over the shear-perforated skin indicates successful delivery of insulin molecules through the pore pathways created by the shear perforation process. The blood glucose concentrations gradually returned to a near normal level in about 5 hours.

FIG. 6b shows rapid increases of plasma insulin concentrations for both pigs as a result of transdermal insulin delivery, reaching the peaks (50 and 90 µIU/ml, respectively) at the end of 50-minute delivery experiment. A comparison of peak plasma insulin concentrations in FIGS. 5b and 6b indicates that transdermal insulin delivery following shear perforation under this experimental conditions delivered a similar amount of insulin into the systemic circulation as subcutaneous injection of 5 IU insulin. The pharmacological responses as indicated by similar blood glucose reductions in both FIGS. 5a and 6a confirm this conclusion.

EXAMPLE 4

Transdermal Glucose Monitoring by Interstitial Fluid (ISF) Sampling through Micropores A swine study was conducted for glucose measurements in both capillary blood and ISF extracted from the micropores generated by the shear perforation procedure as described in Example 3. Briefly, subcutaneous injections of fast-acting insulin (2 IU, Regular Iletin® II, U-100, Pork, Eli Lilly, Indianapolis, Ind.) were administered to four pigs. There was a significant reduction in the blood glucose concentration among these test pigs following the insulin injections. Glucose changes in the blood were monitored periodically using One Touch® Basic glucose meter (LifeScan, Inc., Milpitas, Calif.) on blood samples from the ear vein. ISF samples were obtained by application of a weak suction to the micropores on the skin with an Aspivenin® suction device (ASPIR, Sannois, France). The ISF samples collected throughout the whole experiment were tested for glucose using both a Fast-Take® and One Touch® Basic glucose meter blood glucose meters (LifeScan, Inc., Milpitas, Calif.) as wells as an YSI glucose analyzer(Model 2700 Select Biochemistry Analyzer, YSI Inc., Yellow Springs, Ohio). A calibration procedure was conducted for the two home-use glucose meters (i.e., the One Touch® and FastTake® meters) against the YSI glucose analyzer using aqueous glucose solutions of various concentrations.

After about one hour, intravenous glucose injections (up to 12.5 g of glucose) were given to all the pigs slowly and in small increments in an attempt to increase the blood glucose concentrations in these pigs. The glucose results from the ISF samples measured by the three different glucose analyzers tracked the blood glucose changes following the initial subcutaneous insulin injection, and the subsequent intravenous glucose injection. This experimental result demonstrated that glucose monitoring could be accomplished by: (1) obtaining an ISF sample with a shear perforation and a suction procedure; and (2) measuring the glucose concentration in the ISF sample using a commercially available glucose meter. The glucose concentrations obtained by monitoring the glucose in the ISF samples were also predictive of the blood glucose concentrations.

EXAMPLE 5

Figure 7:
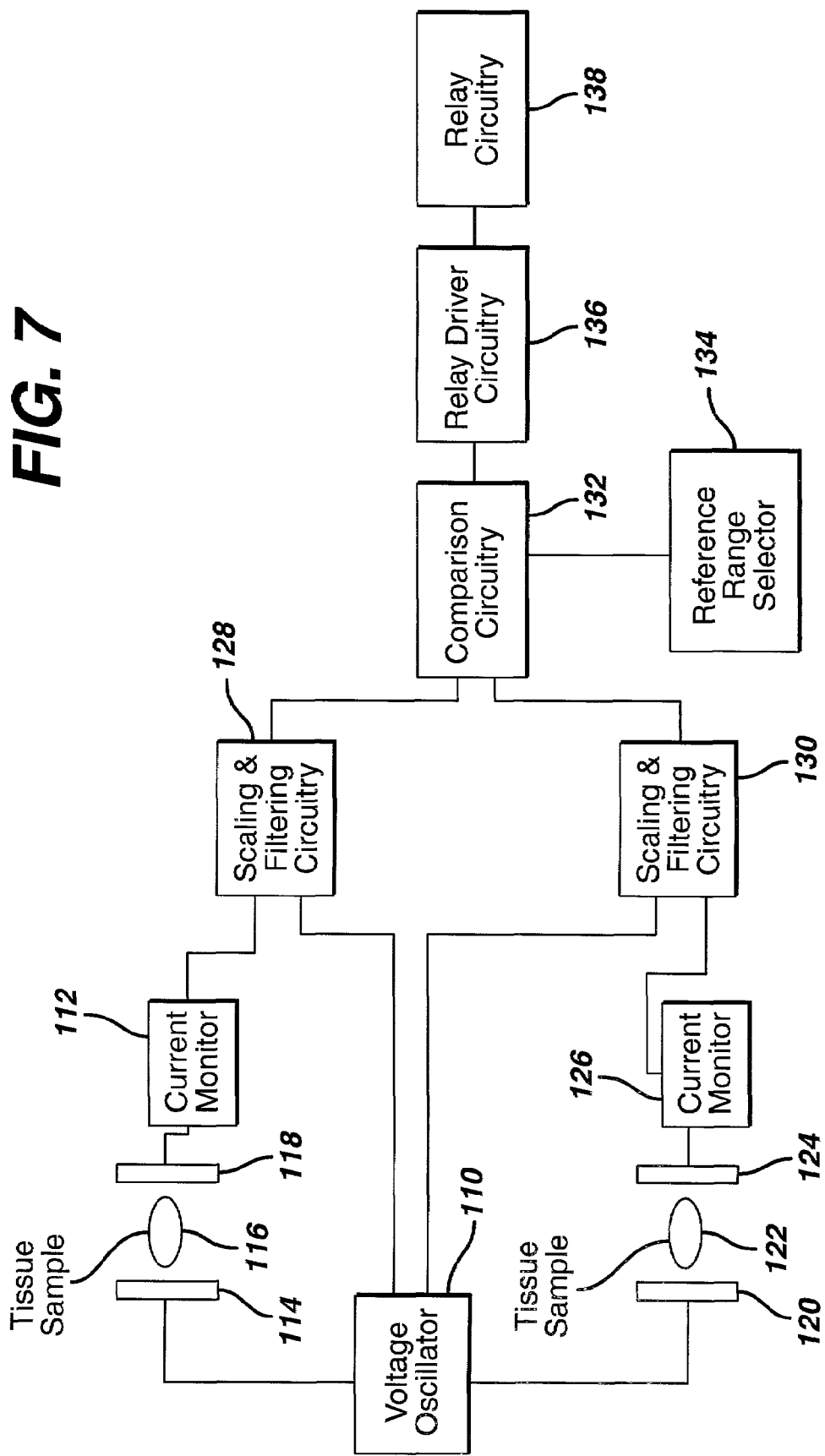
FIG. 7 is a block diagram of an electronic circuit of the impedance sensor and motor control of one embodiment of a shear device.

Electric Circuit of Conductivity Sensors to Activate and Deactivate the Motor of the Shear Device used for Tissue Ablation A block diagrammatic illustration of an embodiment of the invention is shown in FIG. 7. The voltage oscillator 110 produces a sinusoidal signal which provides the voltage input to both the experimental input electrode 114 and the control input electrode 120. The voltage input from the voltage oscillator 110 next travels from experimental input electrode 114 and conyrol input electrode 120 through the experimental tissue sample 116 and control tissue sample 122, respectively. The experimental return electrode 118 and control return electrode 124 complete the electrical circuit containing tissue sample 116 and tissue sample 122, respectively. The experimental current monitoring circuitry 112 detects the current traveling through the experimental tissue sample 116 and outputs a voltage signal to the scaling and filtering circuitry 128 proportional to the magnitude of the current traversing that pathway. In a similar manner, the control current monitoring circuitry 126 provides a voltage to the scaling and filtering circuitry 130 proportional to the amount of current flowing through the control tissue sample 122.

Both scaling and filtering circuits 128 and 130 provide gain control and signal conditioning to the voltage signals obtained from the two current monitoring circuits 112 and 126, respectively. The output from the experimental scaling and filtering section 128 is compared to the output from the control scaling and filtering section 130 by the comparison circuitry 132. The comparison circuitry 132 provides an output polarity based on which input signal is larger than the other. The reference range selector 134 allows one to adjust the magnitude of the signal representing the experimental tissue sample 116 pathway in the comparison circuitry 132. Altering the magnitude of the input to the comparison circuitry 132 from the scaling and filtering circuit 128 allows various trip thresholds for the comparison circuitry 132 to meet in order to activate the relay driver circuitry 136. The motor relay circuitry 138 is activated or deactivated based upon the output of the comparison circuitry 132 and its ability to activate or deactivate the relay driver circuitry 136.

Figure 8A:
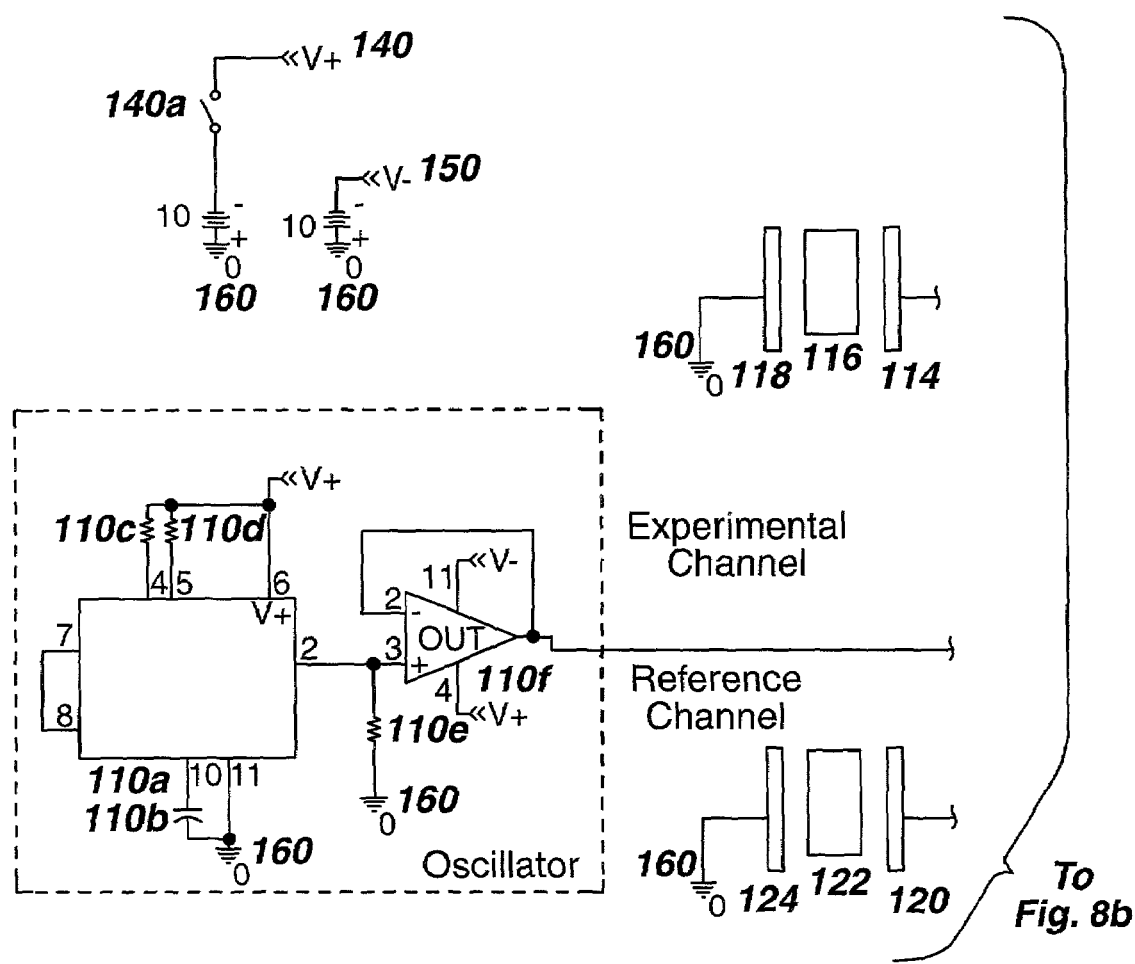
FIG. 8 is an electrical of an electronic circuit of the impedance sensor and motor control of one embodiment of a shear device.
Figure 8B:
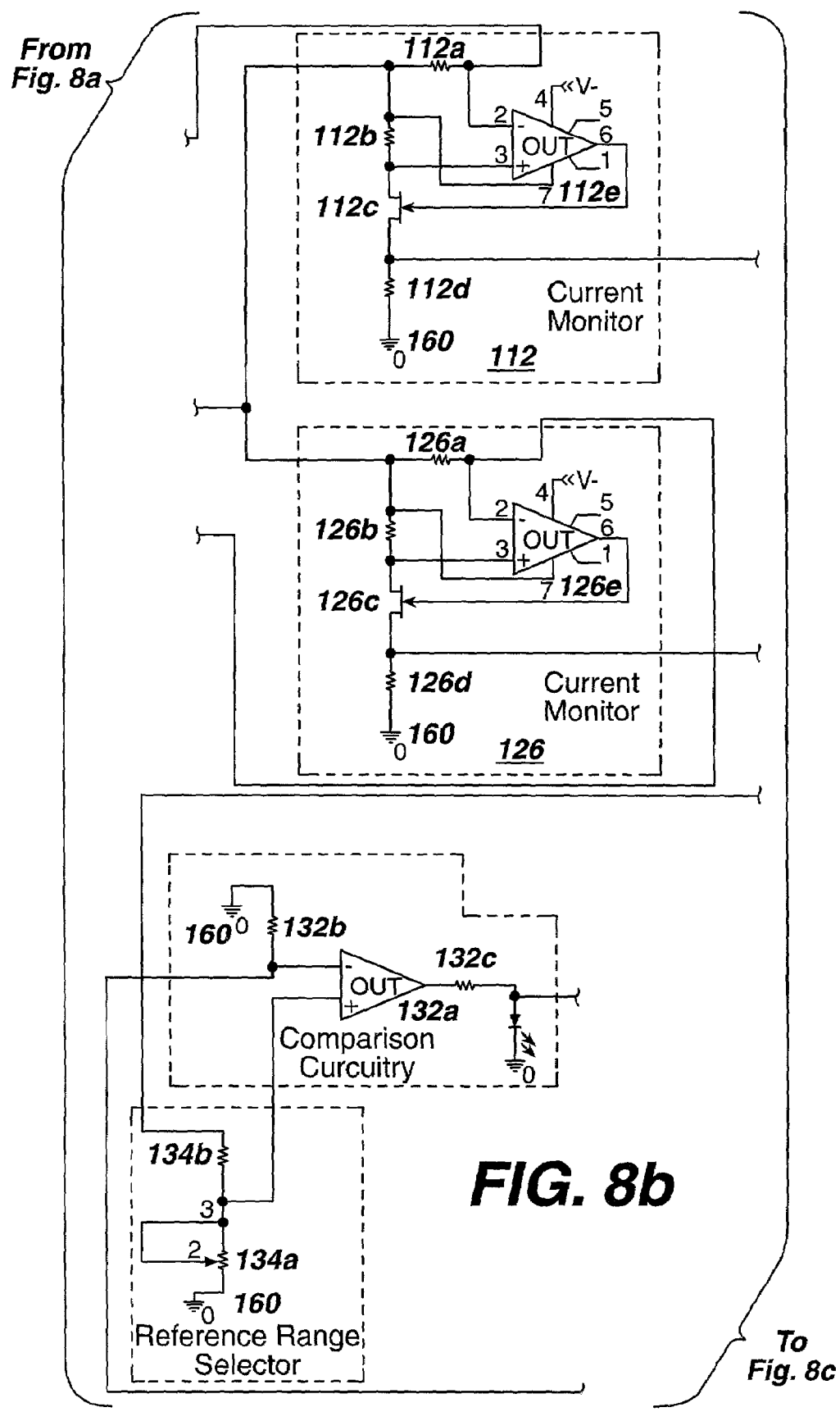
Figure 8C:
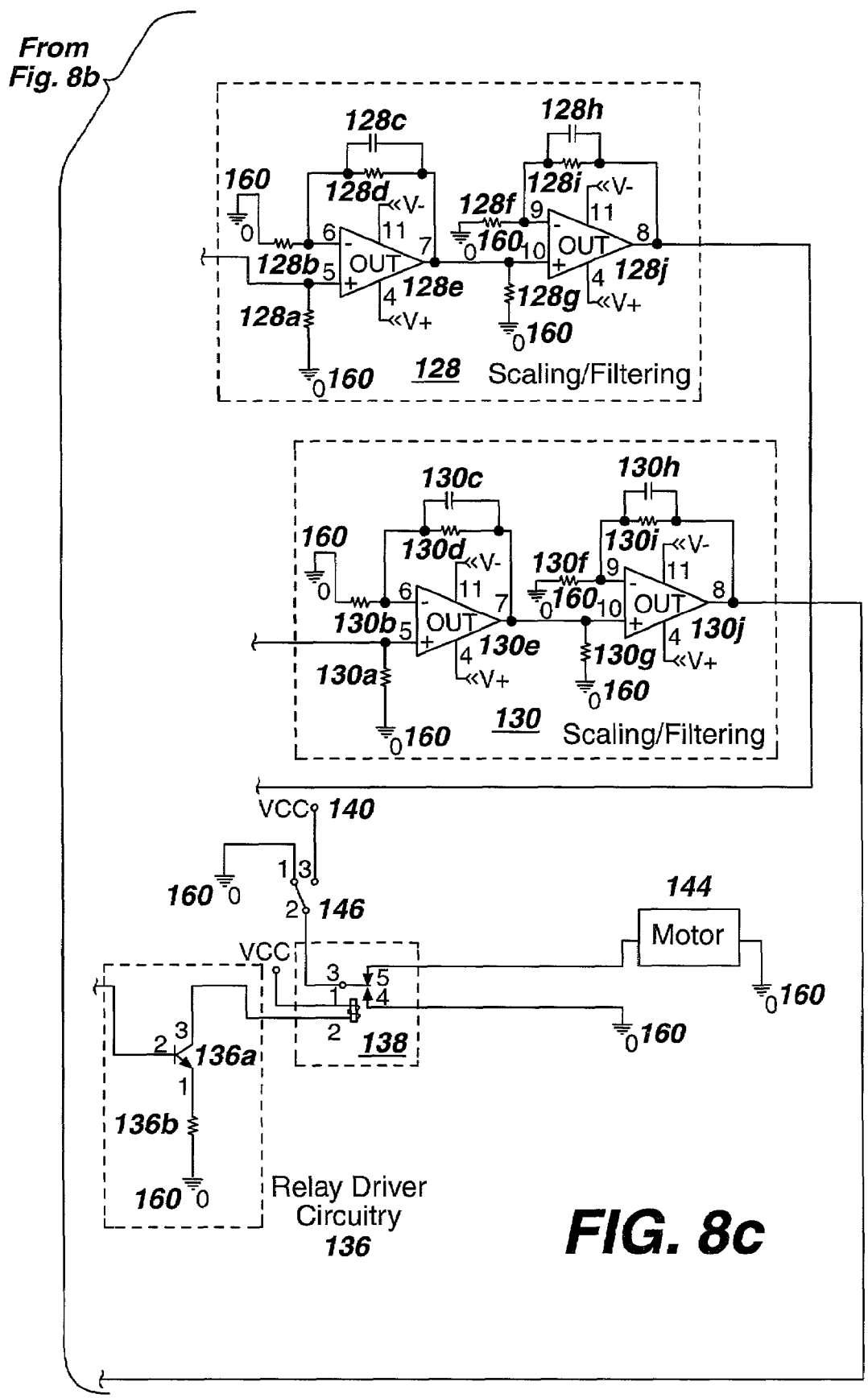

One embodiment of a full diagram of such a circuit is set forth in FIG. 8. The control and impedance sensing circuitry for the mechanical shaving apparatus consists of a combination of Integrated Circuits (IC) including operational amplifiers (Model No. LM324, National Semiconductor, Santa Clara, Calif., USA) oscillators (Model No. ICL8038, Intersil, Irvine, Calif., USA), comparators (National Semiconductor Model No. LM393), and transistors. The operation of these devices is well known. Power is applied to the circuit through the DC supply represented as a battery 140 and ground 160 once the power switch 140a is activated. The negative power supply is also represented as a battery 150. Although the power sources are shown as batteries, it is clear that AC sources with a DC converter could be used instead. Furthermore, upon power-up of the circuit the oscillator IC 110a begins to provide a sinusoidal output at pin 2. Resistors 110c and 110d are set equal to provide a 50% duty cycle while the ratio of resistor 110c and capacitor 110b determine the frequency of the output waveform. Resistor 110e creates an input voltage at the positive input of the operational amplifier 110f which is configured as a traditional buffer. This buffer configuration provides a low source impedance to the remaining circuit components. The output from the oscillator section 110 passes through each of the following two current monitoring circuits.

Current monitor circuits 112 and 126 function identically. This particular current monitoring circuit configuration is well known. This configuration provides an output voltage proportional to the current flowing through the sense resistors 112a and 126a. The transistors 112c and 126c, respectively, provide an equal current between their respective drains and sources which creates a voltage at each source resistance 112d and 126d, respectively, proportional to the current flowing through the sense resistors 112a and 126a. The operational amplifiers 112e and 126e within the current monitoring circuits turn on the transistors 112c and 126c once current begins to flow through the sense resistors 112a and 126a. The sense resistors 112a and 126a are in-line with the tissue samples and connect to the experimental input electrode 114 and the control input electrode 120. The electronic impedance circuit initiated by the oscillator 110 is completed through the tissue samples 116 and 122 by returning to ground 160 through the experimental reference electrode 118 and the control reference electrode 124.

The outputs from the current monitoring circuits 112 and 126 are then filtered and amplified by the scaling and filtering sections 128 and 130 respectively. These sections incorporate the well-known non-inverting operational amplifier configuration to provide gain and signal filtering. Two stages of amplification were used in the scaling and filtering sections due to amplifier bandwidth considerations.

The output from the control scaling and filtering section 130 connects directly with the negative comparitor input 132a of the comparison circuitry 132. The output from the experimental scaling and filtering section 128 connects to a potentiometer circuit contained in the reference range selector circuit 134 which then connects to the positive input of the comparator 132a. The potentiometer 134a and resistor 134b combination alters the amplitude of this voltage signal stemming from the current through the experimental tissue sample 116. Manipulation of these components changes the threshold for comparison between the current traveling through the experimental tissue sample 116 and the control tissue sample 122. Therefore, the comparitor 132a threshold can be set at some multiple of the experimental tissue sample 116 current based on the potentiometer circuit 134a and 134b contained in the reference range selector circuit 134. For example, if the reference range selector circuitry equilibrates the potentiometer 134a and resistor 134b values, then the impedance of the experimental tissue sample 116 must drop by one-half when compared to the control tissue sample in order for the comparator 132a to change state an activate the relay driver circuitry 136.

The output of the comparison circuit 132 is maintained low until the impedance drops in the experimental tissue sample 116 by the appropriate percentage as dictated by the reference range selector circuitry 134. When the appropriate impedance change occurs, a high voltage results at the output of the comparator 132a. The high voltage signal causes the light emitting diode 132d to illuminate thus providing a visual signal that the desired threshold has been met. Resistor 132c functions as a current limiter for the light emitting diode 132d and base of the transistor driver 136a. The relay driver circuit 136 uses an NPN transistor in a typical manner to provide the necessary current to activate or deactivate the motor relay 138. The motor switch 146 initiates the cutting mechanism when the device is in place. Once the appropriate impedance threshold is met, the relay driver circuitry 136 is activated by the output of the comparison circuitry 132 which results in a deactivation of the cutting mechanism.

EXAMPLE 6

Figure 9:
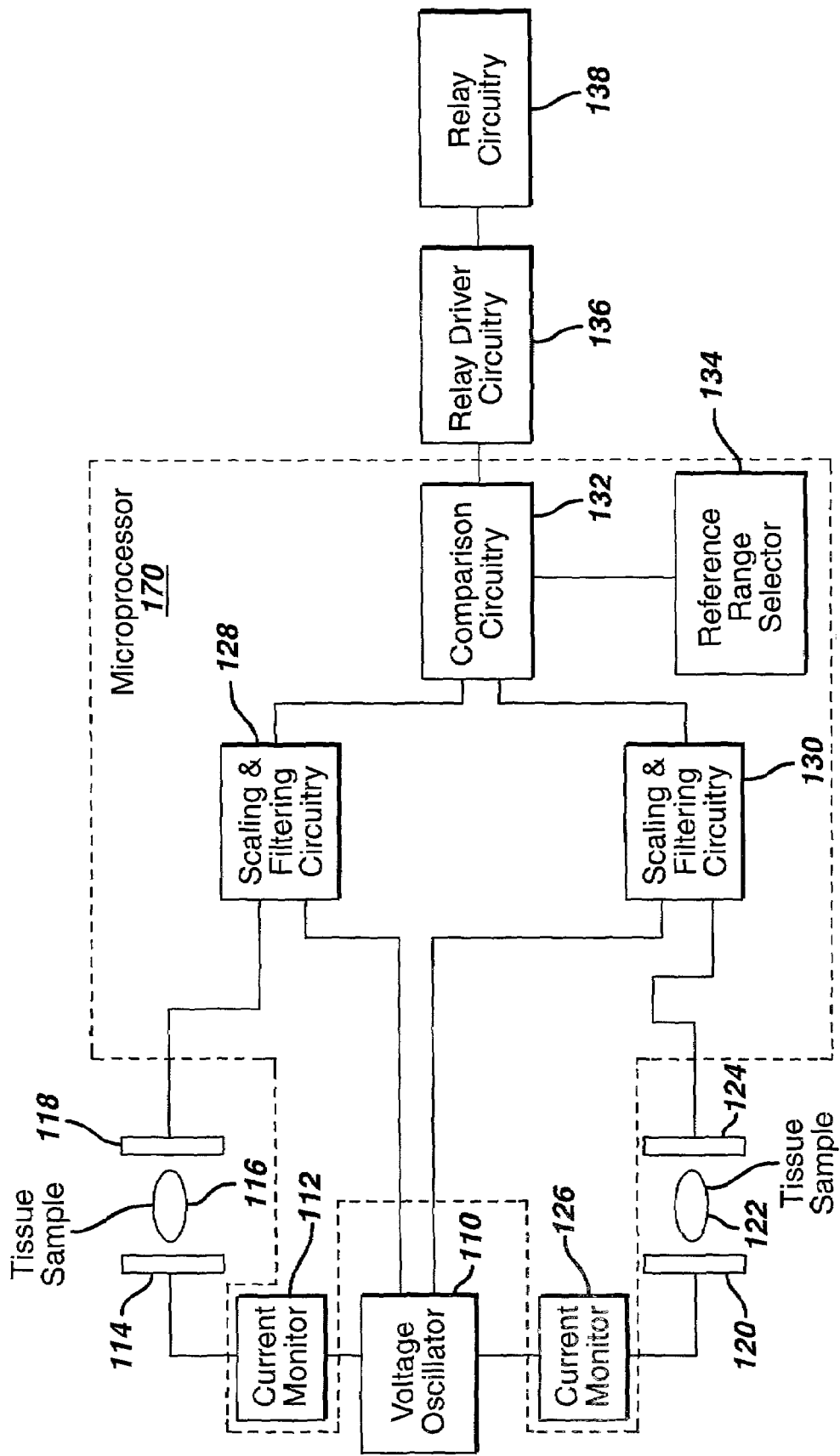
FIG. 9 is a block diagram of an electronic circuit of the impedance sensor and motor control of one embodiment of a shear device containing a microprocessor.

A Microprocessor Based Electric Circuit of Conductivity Sensors to Activate and Deactivate the Motor of the Shear Device used for Tissue Ablation FIG. 9 discloses and alternate embodiment of the invention which uses a microprocessor circuit (Motorola 68HC11 Family of Microcontrollers, Motorola, Inc., Schaumburg, Ill., USA). The microprocessor's program is written in C, C++, or Assembly programming languages. This embodiment shows the microprocessor 170 assuming the roles of many of the components utilized in the previously described analog circuit in FIG. 8. Specifically, the analog-to-digital converter within the microprocessor is used to sample the voltage from the oscillator chip 110 and both the current from the experimental tissue sample 116 and the control tissue sample 122. This allows for continuous monitoring of these parameters. As the voltage and current data is collected, the software algorithm computes the impedance or conductance values of both the control tissue sample 122 and the experimental tissue sample 116. The microprocessor contains a user interface that allows one to input the desired experimental trigger threshold as a percentage of the control tissue impedance. Once the impedance of experimental tissue sample 116 has decreased below the established threshold, the microprocessor will send a signal to activate the relay driver circuitry 136 which deactivates the motor relay 138, thus, turning off the motor to the shearing device. This embodiment has advantages over the analog circuit presented in FIG. 8 as this microprocessor-based circuit continually monitors impedance and or conductance changes, has improved flexibility, conducts mathematical manipulations, and can be programmed for improved safety and control.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method for transporting a molecule through a mammal's mammalian barrier membrane of at least one layer of cells comprising the steps of:
   contacting said mammalian barrier membrane with a sheet of a shear device, the sheet containing at least one opening;
   forcing a portion of said mammalian barrier membrane through the at least one opening;
   ablating said portion of said mammalian barrier membrane forced through the at least one opening with a shear member of said shear device, wherein the shear member ablates said portion of the mammalian barrier membrane by moving over the sheet and the at least one opening; and
   utilizing a driving force to transport said molecule through the ablated portion of the mammalian barrier membrane.

2. A method of claim 1, wherein said shear member is a shear blade.

3. A method of claim 2, wherein said portion of said mammalian barrier membrane is forced through said opening by a pressure force.

4. A method of claim 3, wherein said pressure force is mechanical pressure.

5. A method of claim 3, wherein said pressure force is suction.

6. A method of claim 2, wherein said shear blade moves parallel to said sheet.

7. A method of claim 1, wherein said shear device further comprises a driving unit configured to move said shear member.

8. A method of claim 7, wherein said driving unit is powered manually by a user of the shear device.

9. A method of claim 7, wherein said driving unit is powered by an electric motor of the shear device.

10. A method of claim 7, wherein said shear device further comprises a sensor configured for feedback from said sensor to control said driving unit.

11. A method of claim 10, wherein said sensor is selected from the group consisting of pressure sensor, conductivity sensor, impedance sensor, pH and temperature sensor.

12. A method of claim 11, wherein said sensor is an impedance sensor measuring the impedance of the mammalian barrier membrane.

13. A method of claim 12, wherein the measurements from said impedance sensor are relayed to a microprocessor of the shear device.

14. A method of claim 1, wherein said mammalian barrier membrane is selected from the group consisting of skin, buccal, vaginal, and rectal membranes.

15. A method of claim 1, wherein said mammalian barrier membrane is human skin.

16. A method of claim 1, wherein said driving force is selected from a group consisting of iontophoresis, electroosmosis, reverse iontophoresis, electroporation, phonophoresis, pressure gradients, and concentration gradients.

17. A method of claim 1, wherein said molecule is a pharmaceutical transported through said mammalian barrier membrane into said mammal.

18. A method of claim 17, wherein said pharmaceutical is selected from the group consisting of polysaccharides, peptides, proteins, and polynucleotides.

19. A method of claim 17, wherein said molecule is a vaccine.

20. A method of claim 19, wherein said molecule is a vaccine against Staphylococcus aureus.

21. A method of claim 1, wherein said molecule is transported from within said mammal out through said mammalian barrier membrane.

22. A method of claim 16, wherein said molecule is glucose.

23. A method of claim 1, wherein said shear member moves parallel to said sheet.

24. A method of claim 1, wherein the area of at least one of said at least one opening is about 0.001 to 5 $mm^2$.

* * * * *